(12) United States Patent
Waldmann et al.

(10) Patent No.: US 8,921,104 B2
(45) Date of Patent: *Dec. 30, 2014

(54) METHOD FOR PRODUCING DENDRITIC CELLS

(75) Inventors: Herman Waldmann, Oxford (GB); Paul J. Fairchild, Oxford (GB); Richard Gardner, Oxford (GB); Frances Brook, Oxford (GB)

(73) Assignee: ISIS Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/538,995

(22) Filed: Jun. 29, 2012

(65) Prior Publication Data

US 2013/0171627 A1     Jul. 4, 2013

Related U.S. Application Data

(60) Continuation of application No. 12/841,064, filed on Jul. 21, 2010, now Pat. No. 8,232,100, which is a continuation of application No. 12/326,831, filed on Dec. 2, 2008, now Pat. No. 7,781,213, which is a division of application No. 11/789,669, filed on Apr. 24, 2007, now Pat. No. 7,473,556, which is a continuation of application No. 09/849,499, filed on May 4, 2001, now Pat. No. 7,247,480, which is a continuation of application No. PCT/GB99/03653, filed on Nov. 5, 1999.

(30) Foreign Application Priority Data

Nov. 5, 1998   (GB) ................................. 9824306.6

(51) Int. Cl.
*C12N 5/00*   (2006.01)

(52) U.S. Cl.
USPC .......................................... 435/325; 435/375

(58) Field of Classification Search
USPC ................................................. 435/325, 375
See application file for complete search history.

(56) References Cited

U.S. PATENT DOCUMENTS

| | | | |
|---|---|---|---|
| 7,247,480 B2 | 7/2007 | Waldmann et al. |
| 7,473,556 B2 | 1/2009 | Waldmann et al. |
| 7,781,213 B2 | 8/2010 | Waldmann et al. |
| 8,232,100 B2 | 7/2012 | Waldmann et al. |
| 2002/0131962 A1 | 9/2002 | Waldmann et al. |

FOREIGN PATENT DOCUMENTS

WO           9721802      6/1997

OTHER PUBLICATIONS

Brossart et al. Virus-mediated delivery of antigenic epitopes into dendritic cells as a means to induce CTL. The Journal of Immunology 158: 3270-3276.*
Abbas & Lichtman. Cellular and Molecular Immunology, Philadelphia, P.A., Elsevier Saunders, 1991, p. 249.
Brocker, et al., Targeted Expression of Major Histocompatibility Complex (MHC) Class II Molecules Demonstrates that Dendritic CellsCan Induce Negative but Not Positive Selection of Thymocytes In Vivo, J. of Exp. Med. 185 (33): 541-550, Feb. 3, 1997.
Clontech Catalog information for vector pEGFP-N1, Protocol # PT3027-5, Version # PR29972, pp. 1-3, 2002.
Ellis et al. (1991) Antigen presentation by dendritic cells provides optimal stimulation for the production of interleukin (IL) 2, IL 4 and interferon-gamma by allogeneic T cells. European Journal of Immunology 21(11): 2803-2809.
Genbank Accession No. U55762, submitted Apr. 17, 1996, accessed online, Feb. 15, 2008.
Keller et al., Hematopoietic commitment during embryonic stem cell differentiation in cultureMol. Cell Bio., 13(10): 473-486 (Jan. 1993).
Klug et al., "Genetically Selected Cardiomyocytes from Differentiating Embryonic Stem Cells Form Stable Intracardiac Grafts," J. Clin. Invest., 98:216-224 (1996).
Reeves, M. E., et al. Retroviral transduction of human dendritic cells with a tumor-associated antigen gene. Cancer Research. 1996, vol. 56, pp. 5672-5677.
Senju et al. Generation and genetic modification of dendritic cells derived from mouse embryonic stem cells. Immunogiology, Blood, 2003, vol. 101, No. 9, pp. 3501-3508.
Slukvin, et al. Directed differentiation of human embryonic stem cells into functional dendritic cells through the myeloid pathway. The Journal of Immunology, 2006, 176: 2924-2932.
Steinman, R. M., et al. Identification of a novel cell type in peripheral lymphoid organs of mice. I. Morphology quantitation, tissue distribution. Journal of Experimental Medicine. 1973, vol. 137, pp. 1142-1162.
Brook & Gardner, "The origin and efficient derivation of embryonic stem cells in the mouse," Proc. Natl. Acad. Sci. USA, 97: 5709-5712 (1997).
Brustle et al., "In vitro-generated neural precursors participate in mammalian brain development," Proc. Natl. Acad. Sci. USA, 94:14809-14814 (1997).

(Continued)

*Primary Examiner* — Michael C. Wilson
(74) *Attorney, Agent, or Firm* — Shweta Chandra; Bozicevic, Field & Francis LLP

(57) ABSTRACT

Disclosed are embryonic stem cell-derived dendritic cells, genetically modified immature dendritic cells capable of maturation, as well as methods for the production of such cells. In one embodiment, the cells made be produced by a method comprising the steps of providing a population of embryonic stem cells; culturing the embryonic stem cells in the presence of a cytokine or combination of cytokines which brings about differentiation of the embryonic stem cells into dendritic cells; and recovering the dendritic cells from the culture. In a further embodiment, the cells may be genetically modified.

19 Claims, 19 Drawing Sheets

(56) References Cited

OTHER PUBLICATIONS

Inaba et al. (1993) "Granulocytes, macrophages, and dendritic cells arise from a common major histocompatibility complex class II-negative progenitor in mouse bone marrow" Proc Natl Acad Soc. USA 90:3038-3042.

Melcher et al. (1999) "Adoptive transfer of immature dendritic cells with autologous or allogeneic tumor cells generates systemic antitumor immunity" Cancer Res 59:2802-2805.

Ridgway (2003) "The first 1000 dendritic cell vaccinees" Cancer Invest 21(6):873-886.

Sallusto & Lanzavecchia "Efficient presentation of soluble antigen by cultured human dendritic cells is maintained by granulocyte/macrophage colony-stimulating factor plus interleukin 4 and downregulated by tumor necrosis factor alpha" (1994) J Exp Med 179:1109-1118.

Saudrais et al. (1998) "Intracellular pathway for the generation of functional MHC class II peptide complexes in immature human dendritic cells" J Immunol 160(6):2597-2607.

Smith, Culture and differentiation of embryonic stem cells, J. of Tiss. Cult. Method, 13:89-94, 1991.

Talmor et al. (1998) "Generation or large numbers of immature and mature dendritic cells from rat bone marrow cultures" Eur J Immunol 28:811-817.

Whiteside & Odoux (2004) "Dendritic cell biology and cancer therapy" Cancer Immunol Immunother 53:240-248.

\* cited by examiner

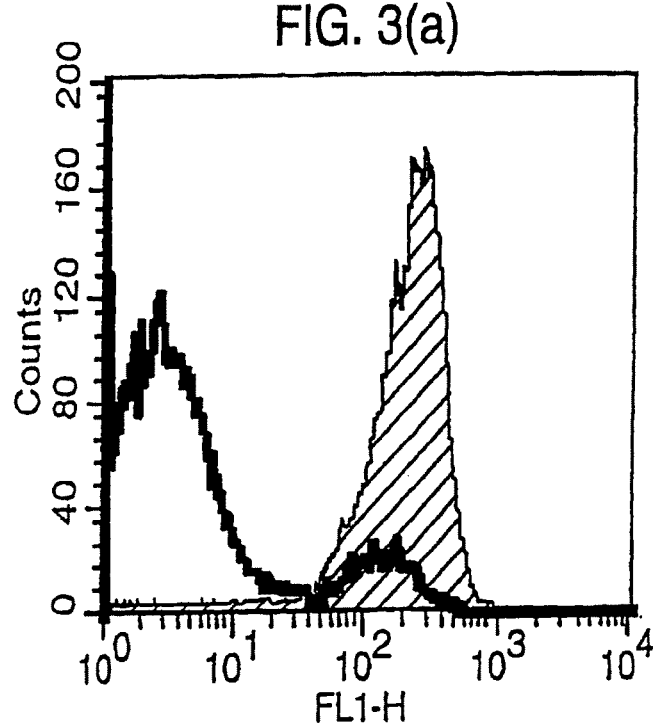
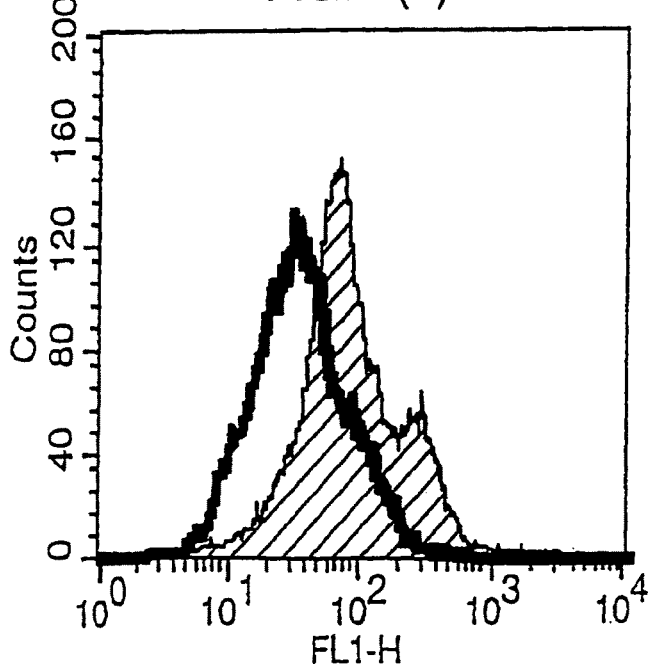

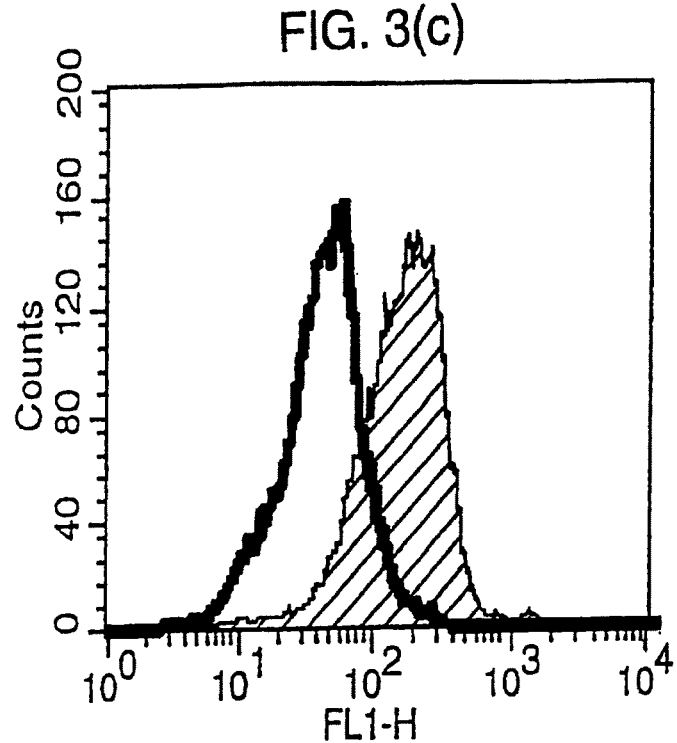
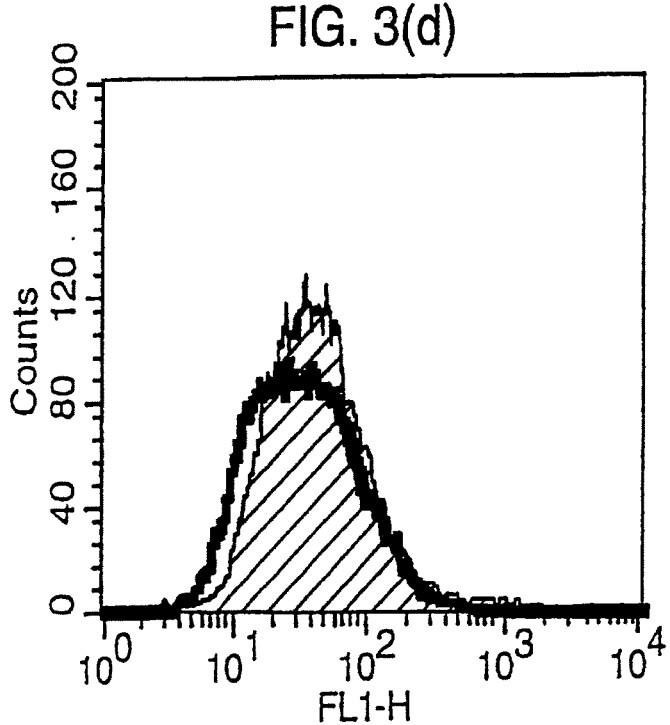

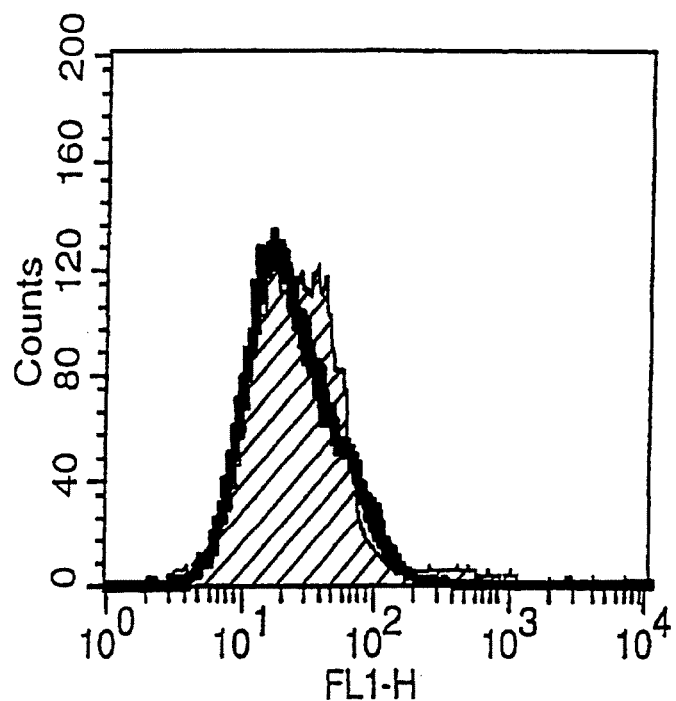

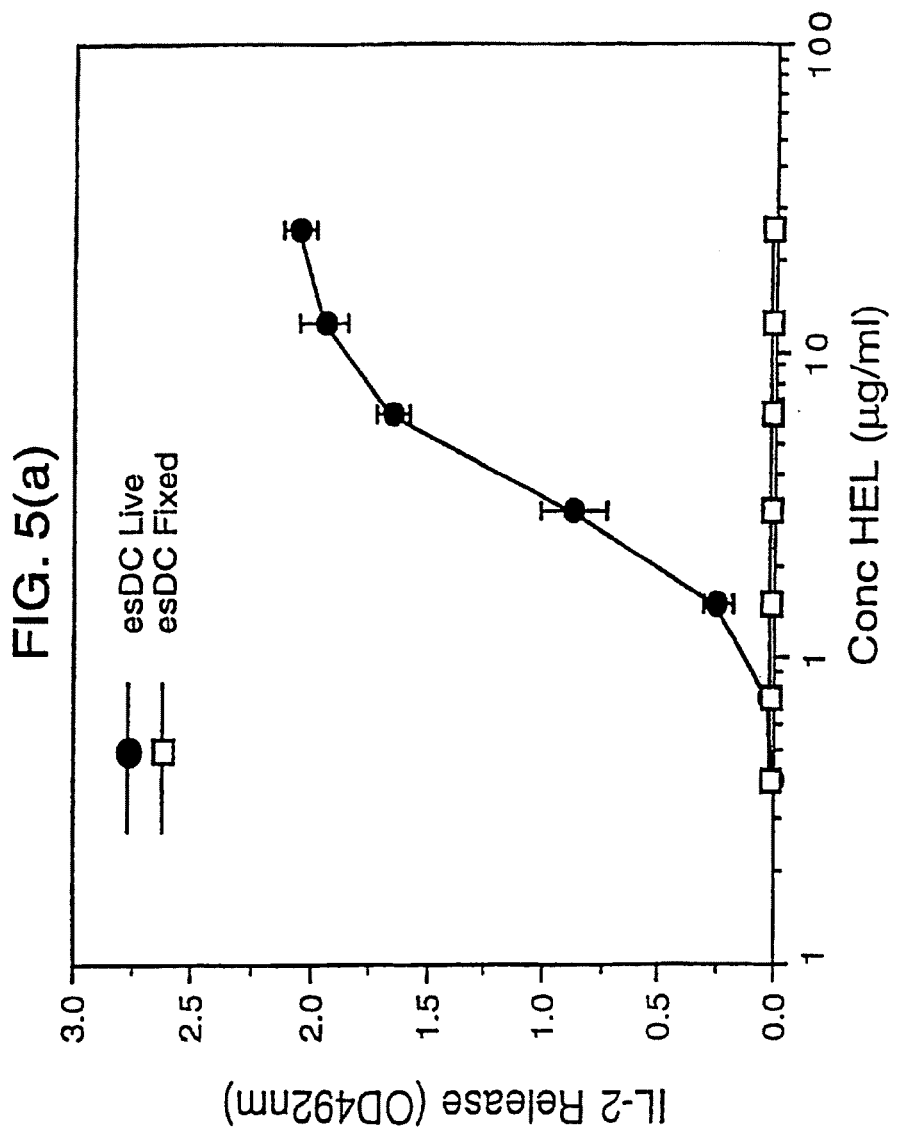

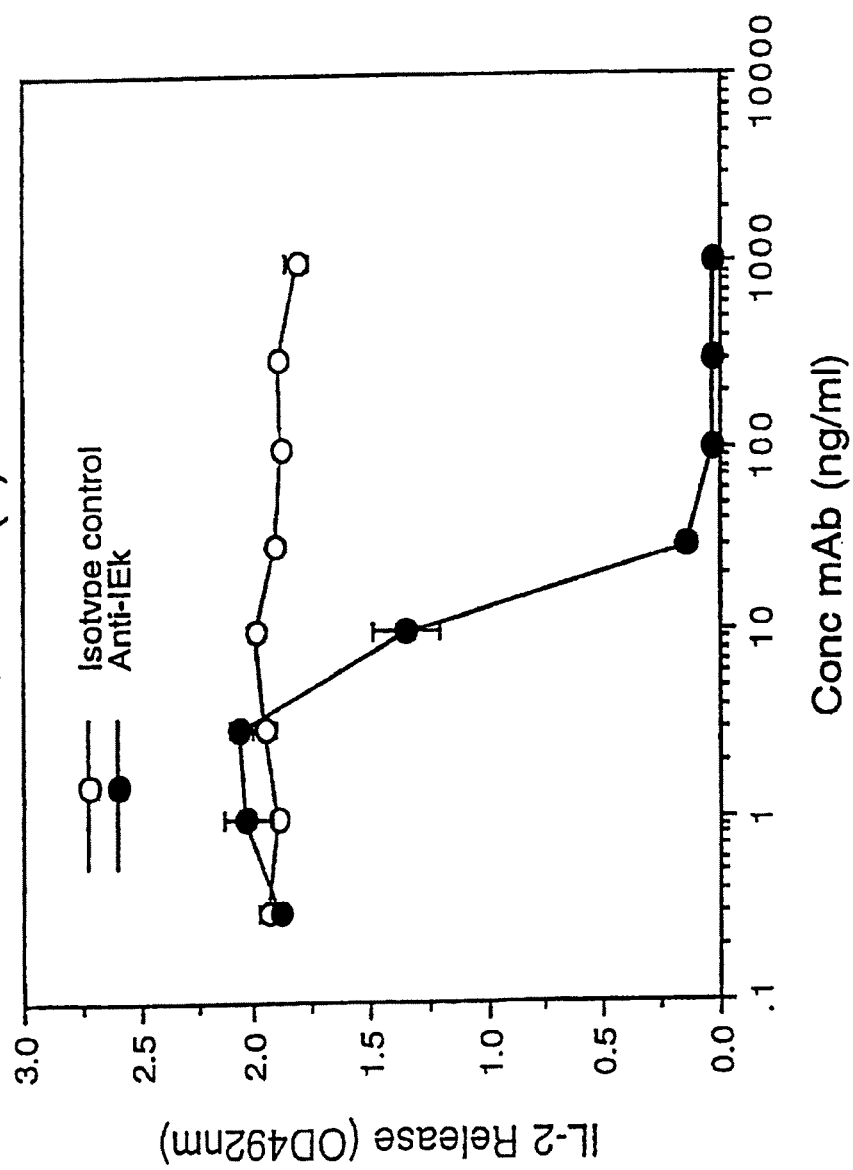

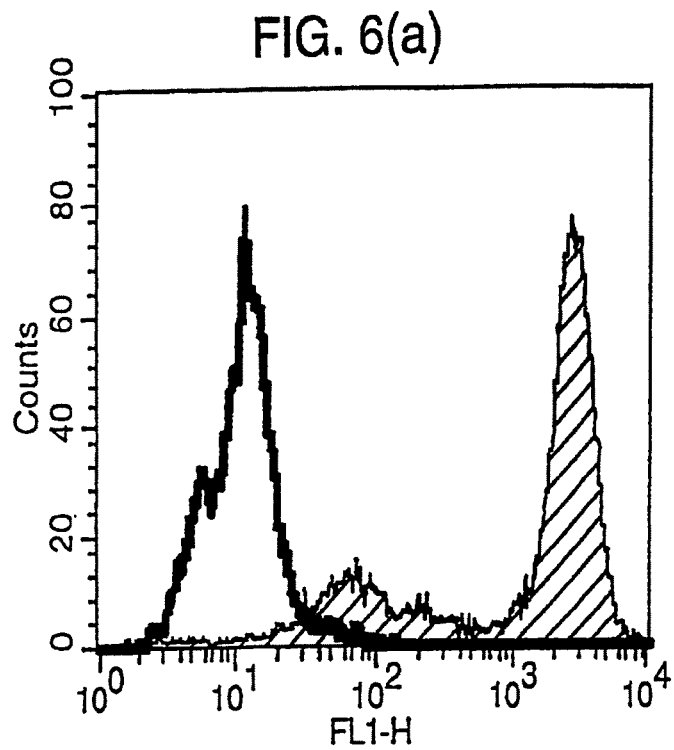
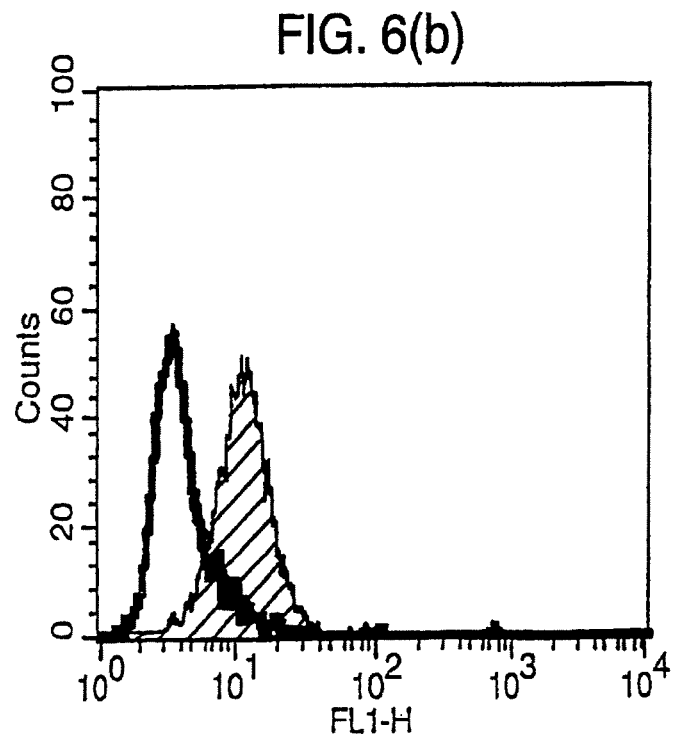

FIG. 10
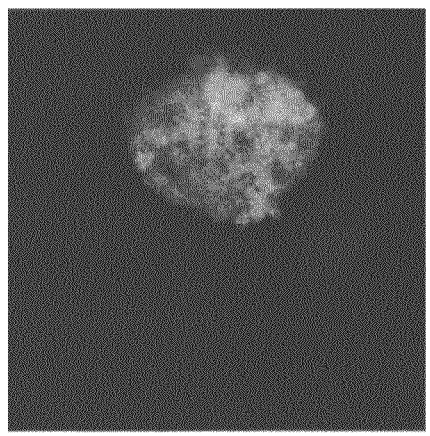
a
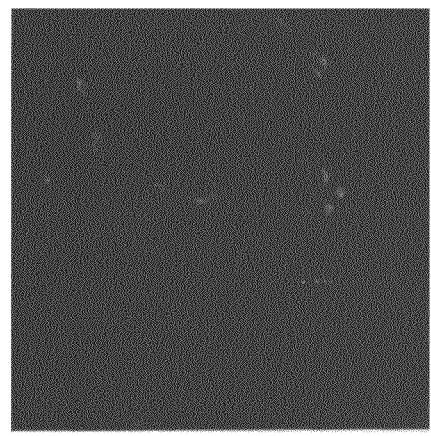
b
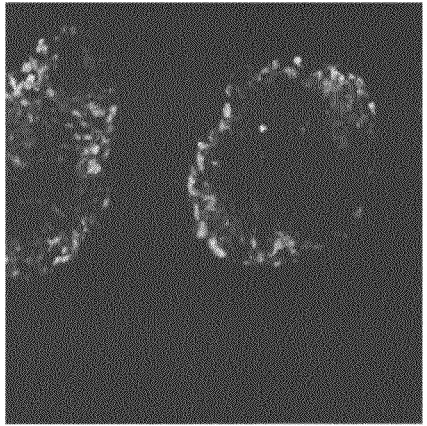
c
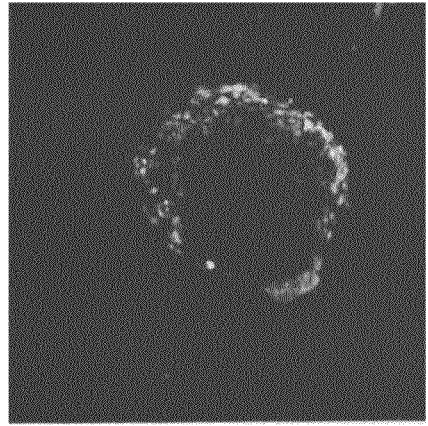
d
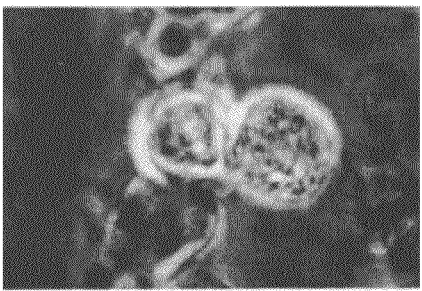
e
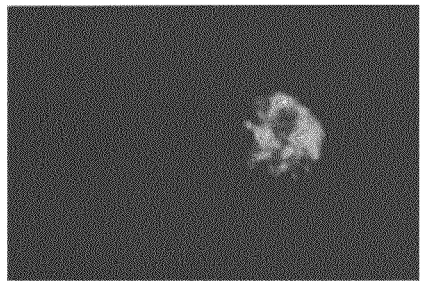
f

METHOD FOR PRODUCING DENDRITIC CELLS

CROSS REFERENCE TO RELATED APPLICATIONS

This application is a continuation of U.S. application Ser. No. 12/841,064, filed Jul. 21, 2010, which is a continuation of U.S. application Ser. No. 12/326,831, filed Dec. 2, 2008, now U.S. Pat. No. 7,781,213, which is a divisional of U.S. application Ser. No. 11/789,669, filed Apr. 24, 2007, now U.S. Pat. No. 7,473,556, which is a continuation of U.S. application Ser. No. 09/849,499, filed May 4, 2001, now U.S. Pat. No. 7,247,480, which is a continuation of International Patent Application No. PCT/GB99/03653, filed Nov. 5, 1999, which application claims priority from GB Patent Application Number 9824306.6, filed Nov. 5, 1998. The entire content of the prior applications is incorporated herein by reference.

The invention relates to a method for the production of dendritic cells from embryonic stem cells and to the dendritic cells so produced. The invention also relates to genetically modified embryonic stem cells and their use in the production of genetically modified dendritic cells; to methods for investigating dendritic cells; and to methods for investigating the function of mammalian genes.

BACKGROUND OF THE INVENTION

The Role of Dendritic Cells in the Immune Response

Dendritic cells (DC) constitute a trace population of leukocytes, originating from the bone marrow but distributed widely throughout most organs of the body, with the possible exception of the brain [Steinman 1991; Banchereau & Steinman, 1998]. The function of DC is largely dependent on their state of maturation, which varies according to their local microenvironment. DC resident within interstitial tissues, such as the Langerhans cells of the skin, are predominately immature, forming a network of cells adapted to the acquisition of foreign antigens following a local microbial challenge.

To perform such a sentinel function, immature DC are competent phagocytes, taking up whole microorganisms and apoptotic cells for processing [Albert et al., 1998a], as well as soluble protein antigens by the endocytic route. Such activity betrays the close lineage relationship between DC and macrophages; indeed the classical DC first described by Steinman and colleagues [1973] are now known to be derived from myeloid progenitors, in common with members of the reticuloendothelial system. What distinguishes DC from macrophages, however, is the nature of their response to an encounter with antigen at a primary site of infection. Inflammatory stimuli, such as the local release of interferon-γ or lipopolysaccharide, induce the maturation of DC precursors [De Smedt et al., 1996; Cella et al., 1997], causing them to lose the ability to acquire further antigens but inducing their migration via the draining lymphatics, to the secondary lymphoid organs [Austyn & Larsen, 1990]. Here they adopt a stimulatory role, presenting the cargo of antigens they acquired in situ, to the repertoire of naive T cells. Their ability to activate T cells that have never before encountered antigen, is a property unique to DC and is a function of the co-stimulatory molecules they express upon maturation, of which CD40, ICAM-1 (CD54), B7-1 (CD80) and B7-2 (CD86) are the best characterized. Furthermore, their propensity to induce a Th1 phenotype among the T cells which respond is due largely to the secretion of cytokines such as IL-12 and IL-18 [Cella et al., 1996; Koch et al., 1996].

Because of their unrivalled ability to stimulate naive T cells in vivo, all immune responses, whether protective or pathogenic, are initiated upon the recognition of antigen presented by DC. Consequently, the potential for modulating the outcome of an immune response by harnessing the function of DC has aroused widespread interest. Indeed, their potential has been successfully exploited in a number of laboratories for enhancing an otherwise inadequate immune response to tumour-specific antigens, resulting in efficient tumour regression [Mayordomo et al., 1995; Celluzzi et al., 1996]. Furthermore, by providing immature DC with a source of chlamydial antigens, Su and colleagues have been able to successfully immunize mice against subsequent infection with Chlamydia [Su et al., 1998], illustrating their likely usefulness in programs of vaccination against infectious agents that have proven difficult to eradicate using conventional strategies.

Over the past few years, the study of immunology has been revolutionized by the discovery that DC may present antigen not only for the purpose of enhancing cell-mediated immunity, but also for the induction of self-tolerance [Finkelmann et al., 1996; Thomson et al., 1996]. This contention has been supported by the characterization of a second lineage of DC derived from a lymphoid progenitor in common with T cells [Wu et al., 1997; Shortman & Caux, 1997]. These cells share with 'myeloid DC' the capacity to acquire, process and present antigen to T cells but appear to induce unresponsiveness among the cells with which they interact, either by preventing their expansion through limiting IL-2 release [Kronin et al., 1996], or provoking their premature death by apoptosis [Suss & Shortman, 1996]. In this respect, lymphoid DC have been reported to constitutively express Fas-ligand which induces cell death among cells expressing its counter-receptor, Fas. These findings have raised the additional prospect of further harnessing the properties of DC to down-modulate detrimental immune responses, such as those involved in autoimmune disease and the rejection of allografted tissues.

In spite of the promise DC hold for exploitation in a therapeutic setting, a number of less-desirable properties of DC have consistently limited progress. Firstly, although it is the immunogenic and tolerogenic function of mature DC which is most amenable to immune intervention, DC exhibit a short life span once terminally differentiated. This has made the prospect of genetic modification of DC less attractive since any benefits gained are necessarily short-lived. Furthermore, primary DC are peculiarly resistant to transfection, confounding most attempts to stably express heterologous genes; indeed the best protocol currently available involves the use of mRNA instead of cDNA for transfection purposes, creating, at best, a transient expression system [Boczkowski et al., 1996]. Although many groups have attempted to circumvent some of these difficulties by generating stable DC lines, the results have been universally disappointing, most putative lines being either retrovirally transformed [Paglia et al., 1993; Girolomoni et al., 1995; Volkmann et al., 1996] or incapable of progressing beyond an immature state [Xu et al., 1995]. Thus none of these provides a useful, renewable source of DC or one that can be genetically manipulated.

Embryonic Stem Cells and their Differentiation

Embryonic stem (ES) cells are derived from the epiblast of advanced blastocysts. The epiblast cells contribute to all cell types of the developing embryo, rather than the extra-embryonic tissues. Individual ES cells share this totipotency but may be maintained and propagated in an undifferentiated state by culturing them in recombinant leukaemia inhibitory factor (rLIF) [Smith et al., 1988], or on a monolayer of embryonic fibroblasts which may act as a potent source of this or related cytokines. Although ES cells may be propagated for a few passages in LIF, for long term culture, fibroblast feeder cells are preferred since ES cells maintained indefinitely in rLIF may lose their differentiation potential.

Unlike primary cultures of DC, ES cells are particularly amenable to genetic modification since they survive even the most harsh conditions for the introduction of foreign DNA, including electroporation. Consequently, ES cells have been used extensively over recent years for the production of transgenic mice and for gene targeting by homologous recombination. Indeed, by introducing a null mutation into selected genes, it has proven possible to generate 'knockout' mice, congenitally deficient in expression of specific molecules [Fung-Leung & Mak, 1992; Koller & Smithies, 1992].

The ability of ES cells to contribute to all lineages of the developing mouse, once reintroduced into recipient blastocysts, is a property which has also proven useful in vitro for the study of lineage relationships [Snodgrass et al., 1992; Keller 1995]. Indeed, a variety of protocols has been devised to encourage differentiation of ES cells along specific pathways. To date, there have been reports of the emergence of cell types as diverse as cardiac muscle, endothelial cells, tooth and neurons [Fraichard et al., 1995; Li et al., 1998]. In addition, differentiating ES cells have been shown to engage in the development of haematopoietic stern cells [Palacios et al., 1995] with the potential to differentiate into erythrocytes, macrophages, mast cells [Wiles & Keller, 1991; Wiles, 1993] and lymphocyte precursors of both the T and B cell lineages [Gutierrez-Ramos & Palacios, 1992; Nisitani et al., 1994; Potocnik et al., 1997].

The Invention

It has now been discovered that DC can be generated by culturing ES cells under certain conditions, more specifically in the presence of IL-3 and optionally GM-CSF. Despite the many studies of haematopoiesis following ES cell differentiation in vitro, the appearance of primary DC (i.e. DC not passaged in culture in their own right) has not previously been reported. Surprisingly, while IL-3 has been used in a number of studies, either alone or in combination with GM-CSF, to induce haematopoiesis within developing embryoid bodies [Wiles & Keller, 1991; Keller, 1995] no DC development has been reported, although a clear effect on erythropoiesis and the development of macrophages and mast cells was routinely observed.

The new findings provide a novel approach to genetic modification of DC which makes use of ES cell differentiation in vitro. In particular, stable lines of genetically modified ES cells can be used to generate mutant DC on demand.

Thus, according to a first aspect of the invention there is provided an es dentritic cell (esDC).

As used herein, the term "es" as applied to dendritic cells (DC) is intended to define dendritic cells which are derived from embryonic stem (ES) cells. Thus, esDC cells may be generated directly from ES cells by culture in vitro (for example, as described herein).

In another aspect, the invention provides a genetically modified immature dendritic cell capable of maturation.

The cells of the invention are preferably human cells. Recent reports of the derivation of human ES cells [Thomson et al., 1998], have stimulated much interest in their exploitation for the generation of terminally-differentiated cell types for use in cell replacement therapy [Gearhart 1998; Keller and Snodgrass, 1999]. For many cell types, however, such as neurons, muscle fibres and oligodendrocytes, their effectiveness in vivo depends on the efficiency with which they can be targeted to the correct anatomical location and site of the original lesion, as well as their propensity to integrate into the host tissue and maintain their physiological competence. For this reason the ES technology now available is far more likely to find an application among populations of cells such as DC that, once reintroduced in vivo, have been shown to migrate under the influence of chemokines, along compex migratory pathways to secondary lymphoid tissues. Importantly, the skilled worker will readily be able to adapt the protocols described herein for the generation of DC from human ES cells, for the reasons explained below.

Firstly, Thomson and colleagues [1998] made use of embryonic fibroblasts from the mouse as a source of feeder cells and found compatibility between the two species, allowing human ES cells to be maintained long-term in an undifferentiated state. Secondly, much is now known about the growth factors required for the differentiation of mature DC in vitro from human haematopoietic stem cells (HSC) [reviewed in Shortman and Caux, 1997]. Significantly, of all the combinations of cytokines tested, only GM-CSF and IL-3 have been found to have the capacity to support DC development from CD34+ HSC, although the efficacy of this protocol is greatly enhanced by the addition of TNF-a to the culture medium, suggesting that this cytokine may also facilitate esDC development from embryoid bodies. Importantly, recombinant human cytokines including GM-CSF, IL-3 and TNF-a are currently available from a number of commercial sources, making the technology readily accessible.

Another approach contemplated by the invention achieves germline competence by harnessing nuclear transfer technology [Wilmut et al., 1997; Wakayama et al., 1998] to permit the transfer of nuclei from human cells to enucleated ES cells of another species (such as ESF116) in order to confer on the nucleus the propensity for germline transmission. Moreover, nuclear transfer in this way may represent a possible solution to the complex ethical concerns surrounding derivation of novel human ES cell lines, making them more widely-available for purposes such as the generation of DC for therapeutic applications.

The invention also provides various medical uses of the cells of the invention, including therapy and prophylaxis. Particularly preferred are immunotherapeutic uses.

The invention therefore provides in another aspect a method for producing dendritic cells which method comprises:
  i) providing a population of embryonic stem cells;
  ii) culturing the embryonic stem cells in the presence of a cytokine or combination of cytokines which bring about differentiation of the embryonic stem cells into dendritic cells; and
  iii) recovering the dendritic cells from the culture.

A cytokine which has been found to be of critical importance in the generation of DC from ES cells in vitro is IL-3. In the presence of IL-3 alone DC develop which exhibit the characteristics of lymphoid rather than myeloid DC.

On the other hand, in the presence of a combination of IL-3 and GM-CSF, larger populations of DC appear which represent DC of myeloid origin.

Thus, the invention is concerned with the production of lymphoid-type and myeloid-type DC under different conditions.

The invention is also concerned with ES cells which are genetically modified and which can pass on the genetic modification or modifications to the resulting DC. Thus, the method according to the invention may employ genetically modified ES cells.

The invention also provides dendritic cells produced by the methods described herein, and genetically modified ES cells useful in the methods described herein including ES cells in which a gene normally expressed in dendritic cells is inactivated, and ES cells transfected with a construct comprising a promoter which is preferentially active in dendritic cells.

In another aspect, the invention provides a method for investigating a mammalian gene, which method comprises generating a test population of dendritic cells from a population of embryonic stem cells and comparing the test dendritic cells in respect of the gene.

BRIEF DESCRIPTION OF THE FIGURES

FIG. 5: shows IL-2 secretion by the T cells in response to antigen presentation by esDC, and inhibition of IL-2 by a mAb to MHC class II; (a) IL-2 secretion by the T cell hybridoma, 2G7.1, in response to HEL presented by live esDC (closed symbols) but not DC that had been fixed first in paraformaldehyde to prevent antigen uptake (open symbols). (b) Stimulation of the 2G7.1 hybridoma is inhibited by the addition of a mAb specific for class II MHC (closed symbols) but not by the addition of an irrelevant species and isotype-matched control antibody (open symbols).

FIG. 10: shows the generation of esDC stably transfected with GFP following introduction of the transgene Into the parent ES cell line. Generation of esDC stably transfected with GFP following introduction of the transgene Into the parent ES cell line. (a) Colony of ESF116 viewed under fluorescent confocal microscopy showing expression of GFP far in excess of the level of autofluorescence associated with the monolayer of embryonic fibroblasts (b). (c)-(d) Embryoid bodies derived from the ESF116.EGFP clone showing retention of the transgene during differentiation. (e)-(f) Representative esDC developing from transfected embryoid bodies viewed under phase contrast (e) and fluorescence microscopy (f) confirming expression of GFP by terminally-differentiated cells.

Figure 1A:
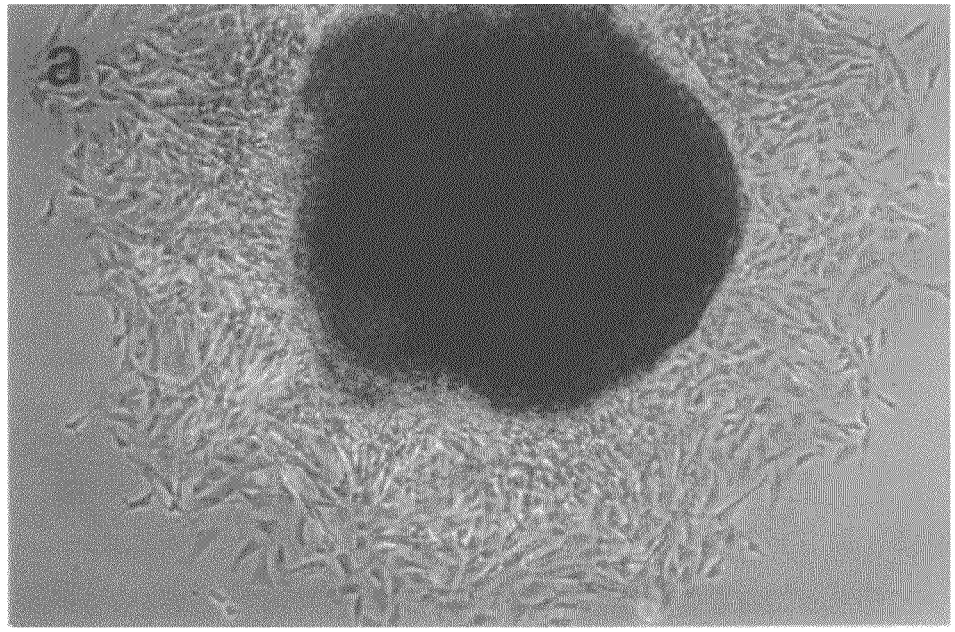
FIG. 1: Phase-contrast micrographs of ES cell-derived dendritic cells. (a) Low power view of an embryoid body 24 hr after plating onto tissue culture plastic, showing the emigration of stomal cells in a radial fashion. (b-c) esDC developing around the periphery of a colony. Note the sharpe demarcation between stromal cells supporting their development and those that fail to do so. (d) Appearance of clusters of esDC (arrows) similar to those apparent in cultures of mouse bone marrow. (e) esDC that have seeded areas of the dish uncolonized by stromal cells. (f) Cultures of putative lymphoid esDC maintained in IL-3 alone.

The source of IL-3 and GM-CSF for use in the invention is not critical; either or both may be provided for example in pure recombinant form, or secreted from a cell line transfected with the gene and expressing the recombinant protein. In the latter case, tissue culture supernatant from the cell line may be used.

S$_0$ far as concentration is concerned, in the presence of murine IL-3 alone murine DC will develop in concentrations as low as 40 U/ml, although 5,000 U/ml is optimal. In practice a concentration of about 1,000 U/ml may be preferable since it is economically more viable and there is still good colony growth of DC at that concentration.

For ES cells in the presence of IL-3 together with GM-CSF, some synergy between the two cytokines may occur. The cell surface receptors for IL-3 and GM-CSF have a common β-chain and therefore quite possibly share some of the same cell signalling mechanisms.

An optimum level of murine GM-CSF for development of murine DC is about 30±5 ng/ml. At that level there is receptor saturation. However, GM-CSF at a concentration as low as 0.1 ng/ml stimulates the production of trace numbers of DC in the presence of 1,000 U/ml IL-3.

Important for the development of DC from ES cells is the formation of embryoid bodies, which are preferably in liquid suspension culture rather than in any semi-solid matrix. It is preferable that embryoid bodies are free-floating for differentiation to proceed optimally.

Embryoid bodies are formed from ES cells which have been removed from the inhibitory effects of LIF. The cells proliferate to form clusters of viable cells, each of which represents an embryoid body and can comprise differentiated or partially differentiated cells of a variety of cell types.

In a particular embodiment of the method according to the invention, embryoid bodies are plated onto tissue culture dishes and exposed to the appropriate cytokine or combination of cytokines to promote development of DC. The embryoid bodies adhere to the surface and give rise to colonies of stromal cells which migrate outwards. After a few days DC develop around the periphery, presumably from early haematopoietic stem cells present in the embryoid bodies. DC which develop in this way can be harvested in substantially pure form, normally with less than 10% contaminating cell types e.g. about 5 to 10% contaminating cell types.

Prior to the formation of embryoid bodies, the ES cells are routinely maintained in an undifferentiated state in the presence of LIF. The LIF is generally provided at this stage in pure recombinant form. However, for maintenance of ES cells in long term culture prior to the formation of embryoid bodies, LIF is preferably provided by culturing the ES cells in the presence of fibroblast feeder cells which secrete LIF and other cytokines.

ES cells for production of DC in the method according to the invention may conceivably be derived from any appropriate mammalian source. Illustrated herein are murine ES cells and DC, but it will be clear that the invention is not necessarily limited to murine cells. ES cells from certain mouse strains are found to be permissive for DC development, while ES cells from other strains are not. However, it will also be clear that the invention is not limited to those permissive strains disclosed herein since it is a straightforward matter to prepare ES cells from other strains and test them for their competence in differentiating into DC.

The apparent inconsistency between the results presented herein and previous studies using ES cells in which no DC were produced or recovered, may reflect a variety of possible factors. These include differences in the protocols employed, an inability in previous studies to identify any resulting DC, and strain differences in the propensity of ES cells to support DC development. In support of the latter possibility, initial studies on the CBA/Ca cell line ESF116 were repeated using a second CBA/Ca line generated in-house (ESF99) and one from 129/Sv mice which is widely used for gene knockout technology and which is commercially available (D3). Interestingly, while ESF99 supported the development of esDC, albeit to a lesser extent than ESF116, D3 failed entirely to do so under the same culture conditions. ES cells generated from other strains can easily be tested for their ability to support development of DC by using the protocols described herein. An additional example of a mouse strain from which ES cells have been shown to support development of DC is C57B1/6 (ESF75).

Certain applications of the invention are discussed in more detail below and in the Examples which follow. It will be clear that the invention is not limited to the specific embodiments described herein. In particular, the genetic manipulation of the ES cells may be in any manner which results in any useful DC phenotype.

Uses of the present invention extend to the fields of tumour immunotherapy and vaccination against infectious agents. Examples include transfection of the parent ES cells with genes encoding tumour-specific antigens or candidate microbial antigens against which a protective immune response is desirable. The endogenous expression of whole protein antigens in this way may harness the potent antigen processing capacity of DC to select the most appropriate epitopes for presentation on both class I and class II MHC, effectively by-passing the need for laborious identification of the epitopes involved. Furthermore, co-transfection of such cells with genes encoding FLIP (accession number: U97076) or bcl-2 (accession number: M16506) may prolong the life-span of esDC administered in vivo. Both molecules have been shown to exert a protective effect, actively interfering with the apoptotic pathways which normally limit DC survival, but in a manner that does not induce their transformation [Hockenbery et al. 1990]. By having their lifespan prolonged in this way, esDC presenting foreign or tumour-specific antigens may provide a chronic stimulus to the immune system. As an additional advantage, the need for adjuvants for the mounting of a powerful protective immune response may be reduced or removed.

The potential for generating lymphoid DC, thought to be important in the maintenance of peripheral self-tolerance, may be exploited in the treatment of autoimmune disease which is characterized by loss of the tolerant state. Certain animal models for autoimmune disease will be useful in investigating the possibilities for treatment. Recently, Goulet and co-workers [1997] reported the isolation of ES cells from the MRL mouse strain susceptible to autoimmunity and demonstrated their germline competence. Such cells may prove useful for the production of esDC of the correct genetic background to permit the development of strategies for immune intervention. Alternatively or additionally, ES cells established from the diabetes-prone NOD mouse could provide useful DC for assessing the potential for immune intervention. A successfully produced ES cell line could be transfected with GAD-65 (accession number: L16980), an autoantigen known to be involved in the aetiology of insulin-dependent diabetes mellitus (IDDM), and induced to differentiate along the lymphoid route. Upon administration in vivo, such cells may actively seek out and tolerize T cells specific for the autoantigen, thereby limiting the extent and progression of tissue damage. Furthermore, by introducing the whole gene encoding GAD-65, all potential epitopes will be presented to the T-cell repertoire, overcoming problems associated with intramolecular determinant spreading [Lehmann et al. 1993]. A similar procedure could be carried out for tolerizing to other autoantigens.

Recently, protocols have been published for the generation of ES cells in which both alleles of a gene have been targeted by homologous recombination, resulting in cells deficient in a given protein [Hakem et al., 1998]. This provides an approach for altering DC function by knocking out candidate genes such as the p40 subunit of IL-12 (accession number: M86671) or the p35 subunit of IL-12 (IL-12 is a hederodimer and at least two genes are involved in its expression). Since this cytokine is fundamental to the establishment of a Th1 response, responding T cells may default to a Th2 phenotype in its absence. Given that Th1 and Th2 cells are mutually antagonistic and that the latter are frequently protective in inflammatory autoimmune conditions [Liblau et al. 1995], IL-12$^+$ esDC may prove effective in inducing immune deviation and modulating the outcome of an ongoing autoimmune response. Should the selection criteria for production of knockout ES cells according to the published protocols prove to be too stringent, alternative approaches to prevent expression or activity of target molecules can be employed. Such approaches include for example antisense constructs, ribozymes or the expression of dominant negative forms of molecules, where available. A dominant negative form of a molecule is an altered e.g. mutated form which blocks the function of the endogenous form of the molecule, for example by binding in its place. Examples of all of these approaches are present in the literature.

Identification of Novel Targets for Immune Intervention

The approaches to immune intervention, outlined above, require prior knowledge of specific genes involved in the immune response and the function they perform. Nevertheless, only a small proportion of the genes that control DC function have been elucidated. The protocols for the development of DC from ES cells in vitro as described herein may, therefore, be exploited for the identification of novel targets for immune modulation which may ultimately prove useful in a clinical setting.

Several approaches to identifying new genes have recently been described, of which the serial analysis of gene expression (SAGE) is perhaps the most powerful [Valculescu et al., 1995]. This methodology permits those genes that are actively expressed by two populations of cells to be compared in a differential manner. It may, therefore, be possible to compare gene expression in embryoid bodies from ESF116, known to support DC development, and those from D3 which fails to do so. Such an approach may define genes involved in the early stages of haematopoiesis which control development of the DC lineage. Alternatively, purified populations of myeloid and lymphoid DC may be compared to elucidate the genes responsible for converting an immunostimulatory DC to one capable of inducing self-tolerance.

While such an approach may highlight important new genes involved in the ontogeny and function of DC, there remains a significant 'gene-function gap', it being considerably easier to identify genes that contribute to a particular phenotype than to elucidate the function of the proteins they encode. As a way of addressing this deficiency, a number of laboratories have pioneered gene-trapping technology [Evans et al., 1997] which seeks to trap genes in an unbiased way and provide the potential for identifying their function. To this end, Zambrowicz et al. [1998] have generated an 'Omnibank' of ES cells in which genes have been randomly targeted for inactivation. Using these cells, knockout mice may be generated which may be screened for specific defects which might betray the function of the targeted gene. Although the production of knockout mice is now well-established, the screening of is large numbers of genes in this way remains an immense undertaking which is likely to be limited by the many logistical constraints. By combining gene trapping technology with our own approach and established readouts for antigen processing and immunostimulation, we may be able to screen rapidly many new genes to identify those that confer on DC their unique properties. This strategy may prove attractive to commercial organizations seeking to identify novel targets for the delivery of DC-specific drugs, so as to intervene in the very genesis of the immune response.

EXAMPLES

Example 1

Derivation and Maintenance of ES Cells from CBA/Ca Mice

Although ES cells may be readily generated from 129/Sv and C57B1/6 strains of mice, strains used more widely in immunological research, such as CBA/Ca and the diabetes-prone NOD mouse, have proven peculiarly resistant. Nevertheless, we have recently developed and published methods for their derivation from such strains [Brook & Gardner, 1997], one of which, ESF116, has been used extensively in these studies and was deposited with the Belgium Coordinated Collections of Microorganisms (BCCM™), Universiteit Gent, Laboratorium voor Moleculaire Biologie—Plasmid Collection, K. L. Ledeganckstraat 35, B-9000 Gent, Belgium on Jul. 29, 1998 under Accession number LMBP 1668CB, under the terms of the Budapest Treaty. ESF116 is karyotypically male, forms chimeras upon injection is into recipient blastocysts and has been found to transmit through the germline.

The ESF116 cell line was isolated from an inbred CBA/Ca female mouse which had been ovariectomized bilaterally and given 1 mg of Depo-Provera (Upjohn, UK) on the afternoon of the third day after mating with a mate mouse of the same strain. Blastocysts arrested in development prior to implantation were recovered in standard HEPES-buffered medium on the morning of the 7th day post-ovariectomy. Each blastocyst was opened up with a pair of solid-tipped, siliconized glass microneedles mounted on Leitz micromanipulator units, which were used to tear open the mural trophectoderm. Once opened, the blastocysts were incubated for 24 min at 4° C. in $Ca^{2+}$- and $Mg^{2+}$-free phosphate-buffered saline (PBS) containing trypsin at 5 mg/ml (Difco) and pancreatin (Difco) at 25 mg/ml. Blastocysts were subsequently returned to the micromanipulation chamber and the trophectoderm of each was opened out with the needles so that the outer surface of the tissue was spread against the coverslip of the chamber. Using one needle to hold the trophectoderm, the other was lowered from the trophectoderm and moved sideways against the exposed inner cell mass (ICM) so as to dislodge the superficial endoderm from the deep epiblast. Once the endoderm had been removed, the same needle was then raised until it made contact with the trophectoderm upon which it was moved sideways, so as to scrape the epiblast gently from the overlying trophectoderm [Gardner, 1985]. Both the initial opening of the blastocysts and their dissection was performed with the microscope stage cooled to 5° C. Once isolated, the epiblast tissue from each blastocyst was pipetted into the individual wells of a four-well tissue culture plate (Nunclon), that had been seeded with mitotically-inactivated primary embryonic fibroblasts the previous afternoon and irrigated with fresh ES cell medium shortly before the epiblasts were explanted.

After culturing for 6 days, individual colonies were picked from the dish using a pulled pasteur pipette, dissociated in a drop of trypsin-EDTA and replated into a fresh well of feeder cells. The resulting colonies were cultured for a further 3 days before the contents were passaged into a 35 mm dish containing mitotically-inactivated embryonic fibroblasts and labelled passage 1. The cells were further expanded into a 25 $cm^{2+}$ tissue culture flask after 2 days, passaged into two fresh flasks 2 days later and thereafter passaged consistently every 3 days.

For routine maintenance of the ESF116 cell line, a stock of embryonic fibroblast feeder cells was prepared from C57B1/6 embryos excised at day 12-13 of gestation. Embryonic tissues, with the exception of the head and liver, were finely minced with a sterile surgical blade in PBS supplemented with 2.5% trypsin (Gibco) and 0.02% EDTA. After transferring to a universal tube, the suspension was placed in a waterbath at 37° C. for 5 min and further dissociated by vigorous shaking. After standing for 5 min, undissociated tissues were found to sediment while unwanted lipids and fats rose to the air-liquid interface. The cell suspension between these two layers was harvested and transferred to a tube containing complete medium (DMEM supplemented with 10% FCS, 2 mM L-glutamine and $5 \times 10^{-5}$M 2-mercaptoethanol) to halt the action of the trypsin. Three serial extractions were performed using trypsin-EDTA and the resulting cell suspensions pooled and pelleted in a bench-top centrifuge. The pellet was resuspended in complete medium and distributed equally among four 75 $cm^2$ tissue culture flasks. After reaching confluency, the monolayers of fibroblasts were passaged into four 150 $cm^2$ flasks to permit their expansion. Once confluent, the fibroblasts were harvested, resuspened in complete medium containing 10% DMSO, aliquoted into cryotubes and stored frozen under liquid nitrogen until required.

Before use as feeder cells for routine maintenance of ESF116, embryonic fibroblasts were mitotically inactivated by culturing for 2 hr in medium containing 10 µg/ml of mitomycin C (Sigma). The cells were washed in PBS, harvested using trypsin-EDTA and distributed among 25 cm$^2$ tissue culture flasks. The fibroblasts were incubated for at least two hours to allow them to adhere to the plastic and form a confluent monolayer. ESF116 cells were seeded onto the awaiting feeder layers by forming a single cell suspension using trypsin-EDTA and producing a range of dilutions in 'ES medium' consisting of DMEM supplemented with 15% FCS, 1 mM sodium pyruvate, 2 mM L-glutamine and 5×10$^{-5}$ M 2-mercaptoethanol.

Example 2

Generation of DC from ESF116

Prior to differentiation of ESF116 in vitro, the cells were cultured free from fibroblast feeder cells by passaging twice in succession in 12.5 cm$^2$ flasks precoated with 0.1% gelatin in PBS to promote their adherence. Cells were maintained in an undifferentiated state during this period by the addition of 1000 U/ml of rLIF to the culture medium. Since, under these conditions, the ESF116 cells expanded rapidly but the contaminating fibroblasts remained mitotically inert, the latter were eventually lost by serial dilution. Pure populations of ESF116 were subsequently harvested by trypsinization, washed and plated onto 90 mm dishes of bacteriological plastic (Sarstedt) at a density of 3-5×10$^5$ cells per dish in 20 ml of complete medium lacking rLIF. Under these conditions, the ESF116 cells failed to adhere to the bacteriological plastic but remained in suspension where they continued to proliferate, forming embryoid bodies. These spheres continued to increase in size, becoming macroscopic at approximately day 4 of culture and adopting a cystic appearance by day 10-12. In the absence of exogenous LIF, the embryoid body has been shown to provide an ideal microenvironment in which differentiation proceeds in a manner and with the kinetics expected of the early mouse embryo [Keller et al., 1993; Schmitt et al., 1991].

After 14 days in culture, the embryoid bodies were transferred to a 50 ml test tube and allowed to sediment under unit gravity before being washed twice in fresh medium to remove unwanted debris. The embryoid bodies were plated at low density onto 90 mm tissue culture dishes (Corning) in 20 ml of ES medium further supplemented with 1000 U/ml of recombinant murine IL-3 (R&D Systems) and 2% (v/v) tissue culture supernatant from is the X63 cell line transfected with the murine gene encoding GM-CSF. The final concentration of GM-CSF was judged to be approximately 25 ng/ml in bone marrow proliferation assays in which a standard dose-response curve had been constructed using recombinant GM-CSF.

Figure 1B:
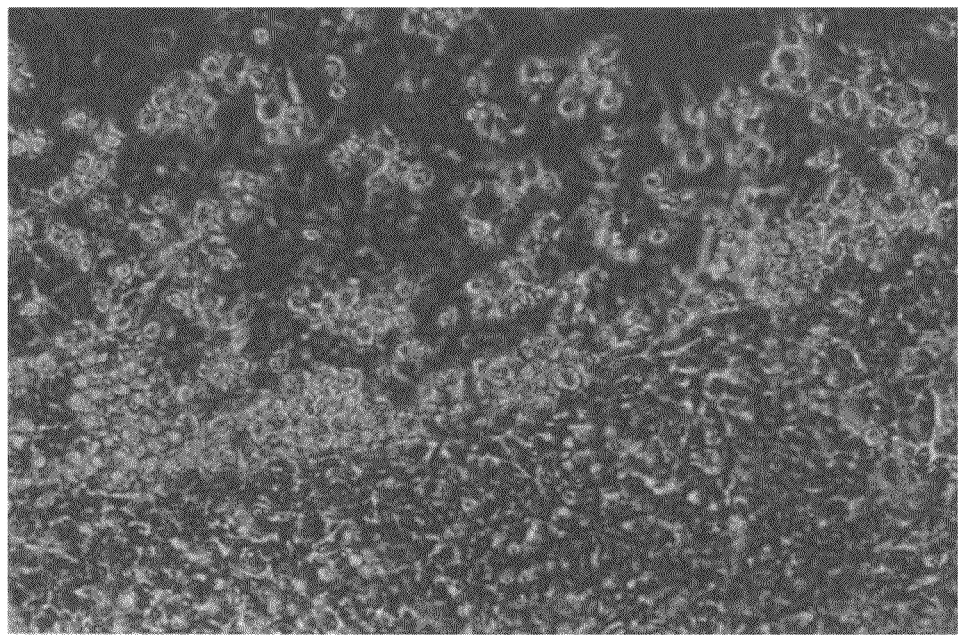
Figure 1C:
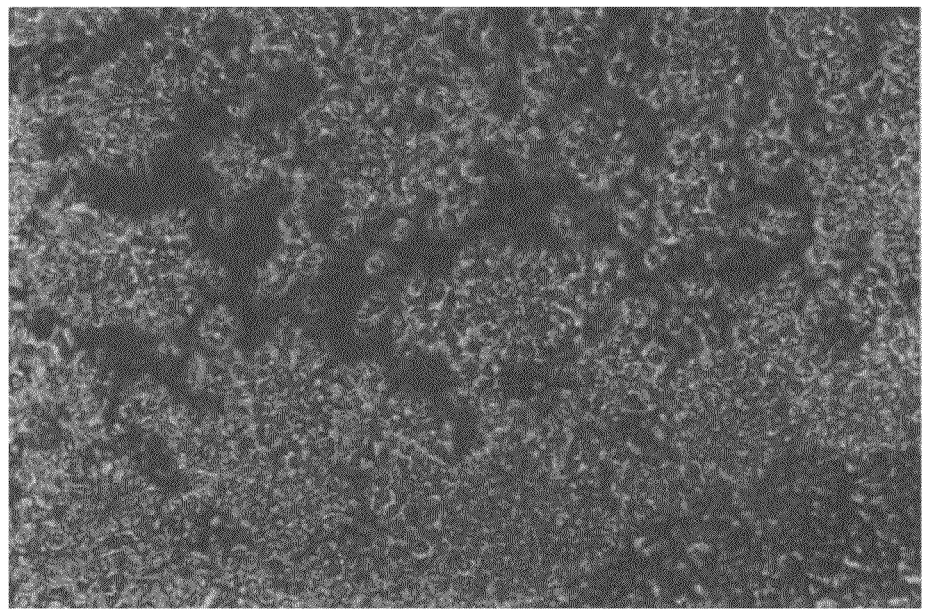
Figure 1D:
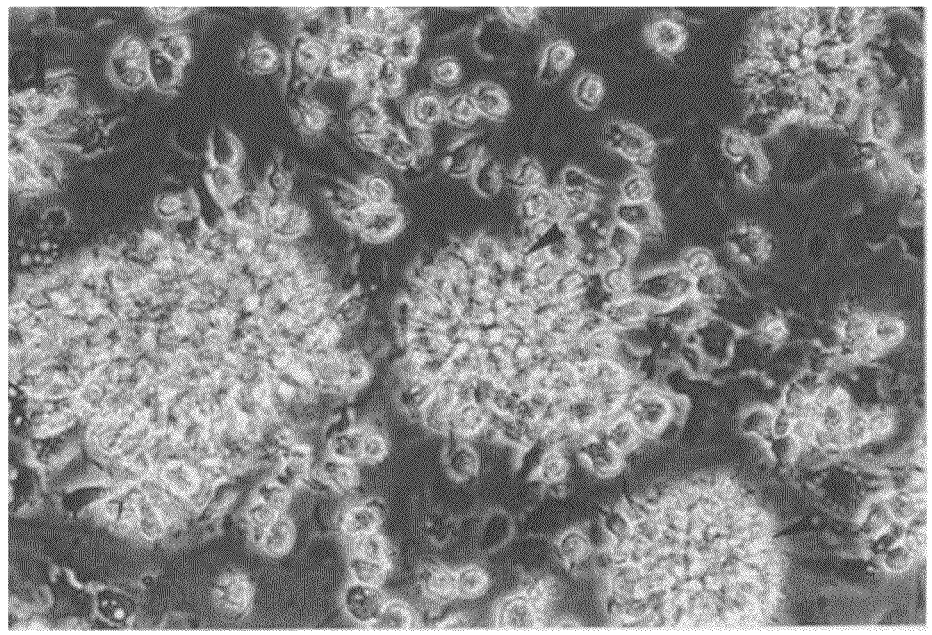
Figure 1E:
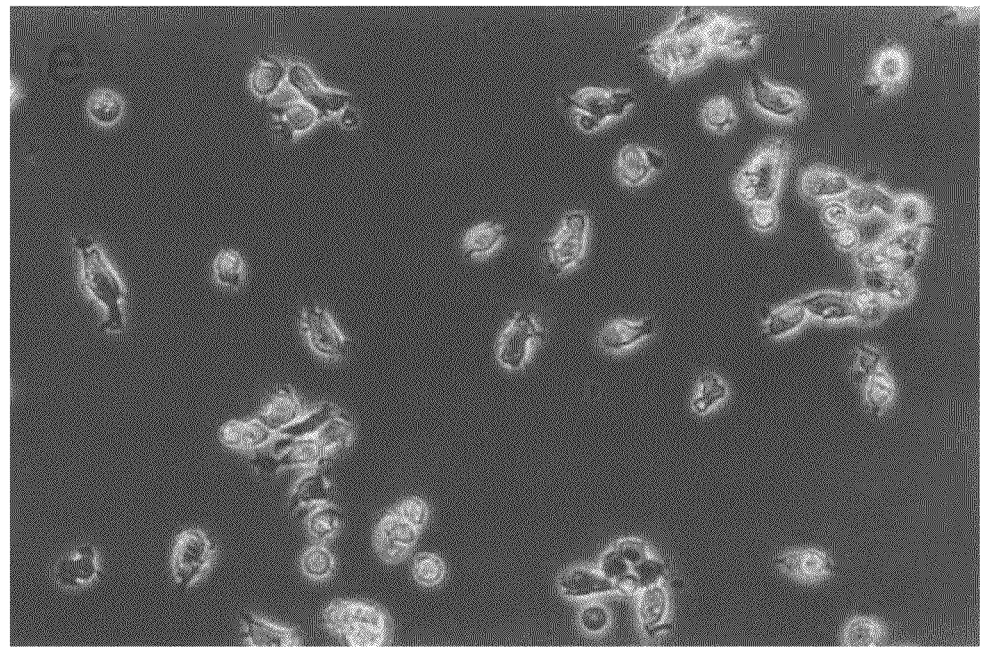
Figure 2A:
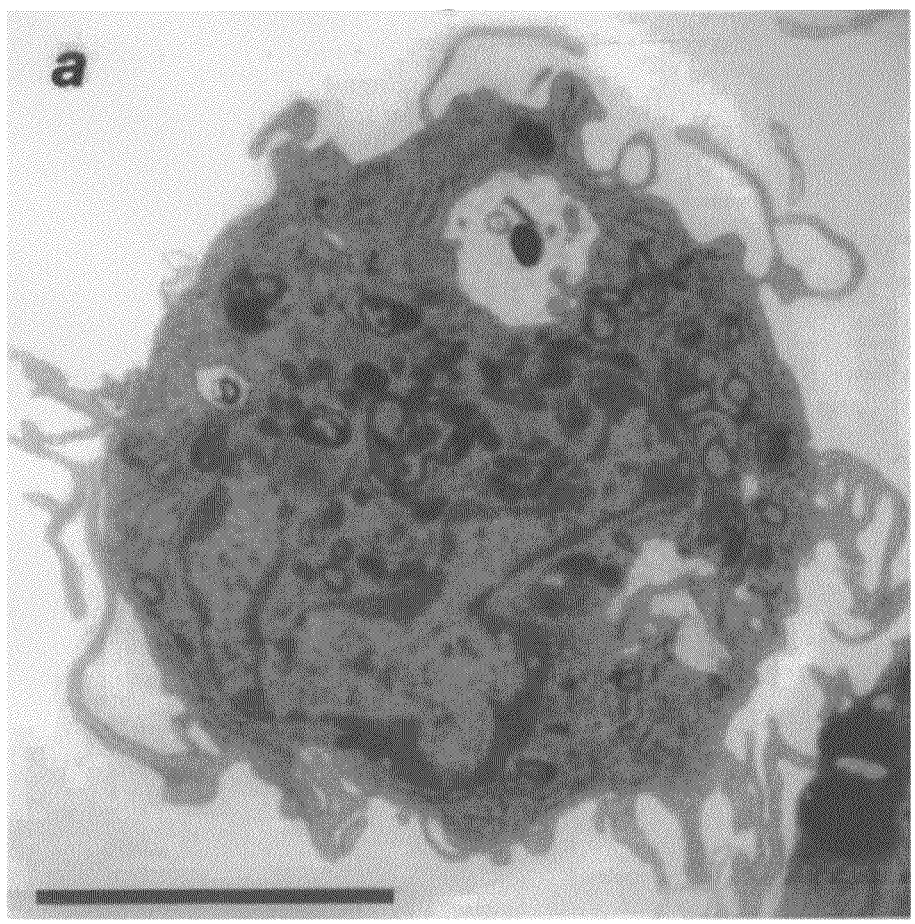
FIG. 2: shows electron micrographs of esDC cultured in GM-CSF and IL-3; Electron micrographs of esDC cultured in GM-CSF and IL-3 showing typical DC morphology (a) and a propensity to phagocytose apoptotic cells (b), consistent with their immature phenotype. The bar represents 5 μm.
Figure 2B:
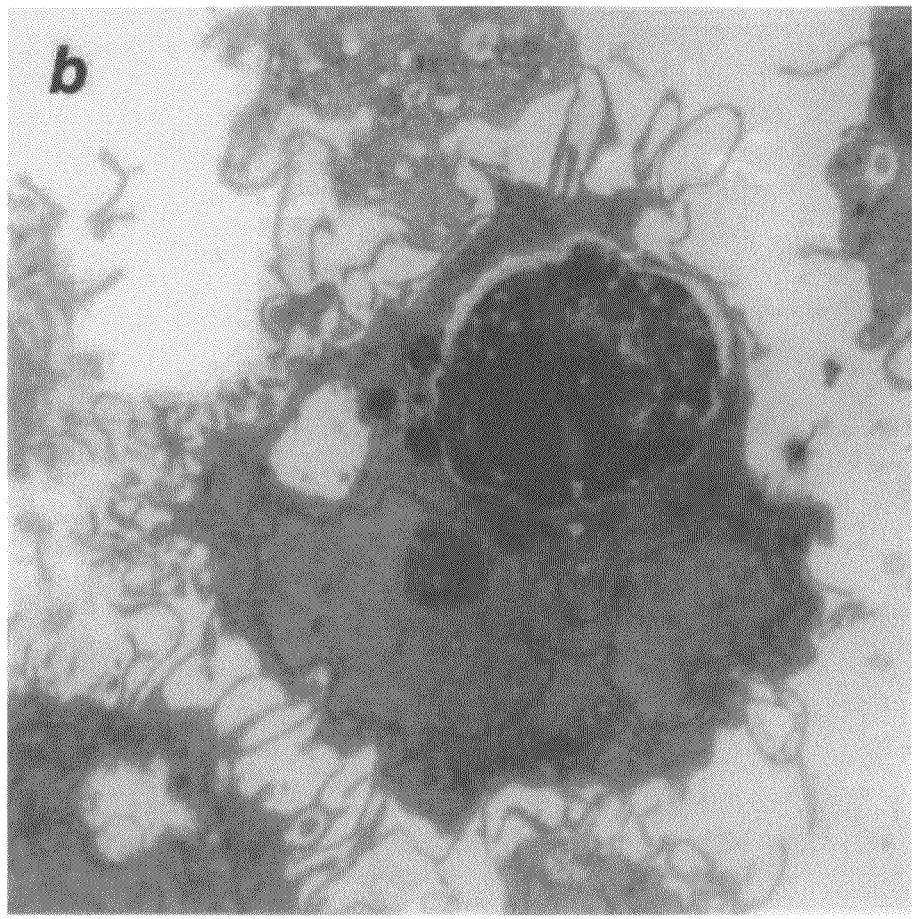

After overnight culture at 37° C., a proportion of the embrycid bodies was found to adhere to the plastic and give rise to colonies of stromal cells, emigrating outwards in a radial fashion (FIG. 1a). By approximately day 4 of culture, cells bearing distinctive DC morphology consistently appeared around the periphery of the stromal layer, the area of DC growth being sharply demarcated (FIG. 1b-c). In this peripheral location, DC continued to proliferate and accumulate, eventually forming the large clusters (FIG. 1d) characteristic of DC generated from bone marrow precursors. With time, DC were found to seed those areas of the dish still free of underlying stroma, where their dendritic morphology was particularly apparent (FIG. 1e). Under transmission EM, these cells showed the ultrastructural features of early DC (FIG. 2a); indeed the detection of cells which had apparently phagocytosed apoptotic cells from their local environment (FIG. 2b) provides further circumstantial evidence of their identity as immature DC [Albert et al. 1998b].

ES cell-derived DC (esDC) could be harvested by gentle pipetting and isolated from unwanted debris by passage of the cell suspension over a 70 µm cell filter (Falcon). Harvesting of esDC in this manner left intact much of the stromal layer which supported the growth of successive cohorts of DC: indeed, cultures have been maintained in our laboratory for at least 5 weeks, during which the cells were routinely harvested for use in experiments. This protocol therefore gives rise to long-term cultures of DC, overcoming many of the difficulties encountered when isolating DC from primary tissues.

The requirement for GM-CSF in the generation of esDC is in accordance with universal findings of its involvement in the development of DC belonging to the myeloid lineage. What is surprising, however, is the inability of this cytokine to support DC development from ES cells in isolation, although GM-CSF alone is highly effective in the generation of large numbers of DC from bone marrow [Inaba et al, 1992]. Furthermore, the need for IL-3 in DC ontogeny is unexpected, although not entirely without precedent. A trace population of CD4 positive T cells known as "plasmacytoid T cells" which have remained enigmatic for many years, have recently been shown to develop the characteristics of DC in the presence of interleukin-3 (IL-3) [Grouard et al. 1997]. IL-3 has been shown to sustain an early population of haematopoietic progenitor cells [Sonada et al., 1988], upon which granulocyte macrophage colony stimulating factor (GM-CSF) may act to induce differentiation along the DC pathway: in the absence of this progenitor, GM-CSF appears ineffectual.

Example 3

Generation of DC from ESFI 16 without GM-CSF

Figure 1F:
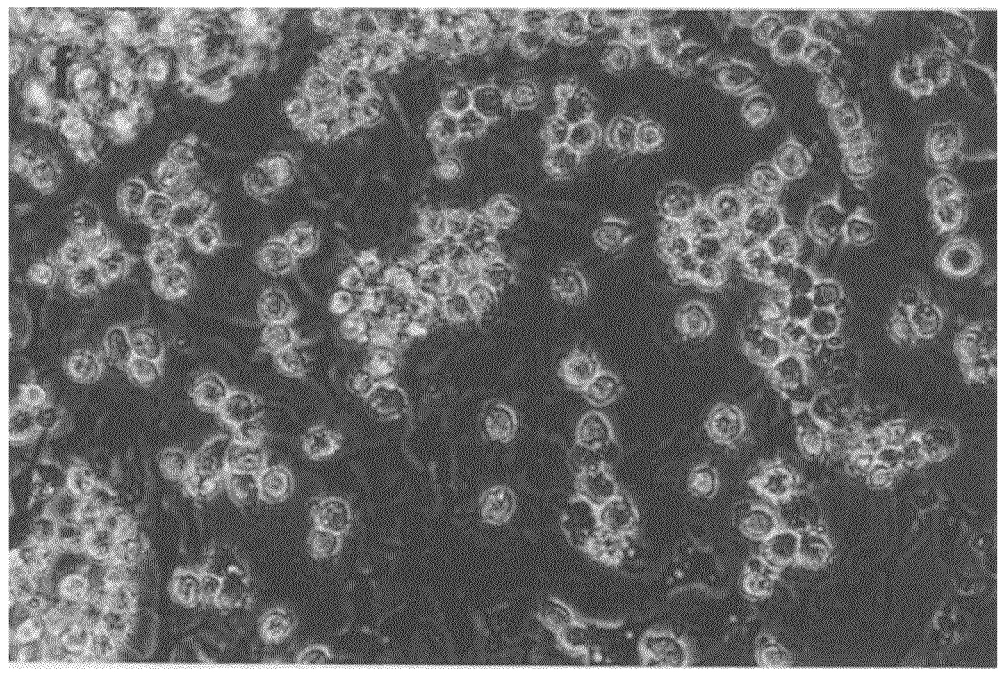

Whereas IL-3 is indispensable for the generation of esDC, the requirement for GM-CSF does not appear to be absolute. Embryoid bodies generated as described in Example 2 and plated onto tissue culture plastic in complete medium containing 1000 U/ml of IL-3 alone, supported a trace population of cells, in the usual peripheral location, bearing dendritic morphology [FIG. 1f]. These cells failed to accumulate to the numbers apparent in cultures described in Example 2 supplemented with GM-CSF and appeared with delayed kinetics after plating. These cells have a limited functional potential in conventional assays of DC activity (see below). Together with their ability to develop in the absence of GM-CSF, this suggests that these cells represent lymphoid rather than myeloid DC, since the lymphoid lineage is known to be independent of GM-CSF [Saunders et al., 1996]. Thus, we have succeeded in defining the conditions for growth of primary DC of myeloid origin and primary DC which exhibit characteristics of lymphoid DC, from ES cells in vitro.

Example 4

Characterization of ES Cell-Derived Dendritic Cells

1. Phenotype

Figure 3E:
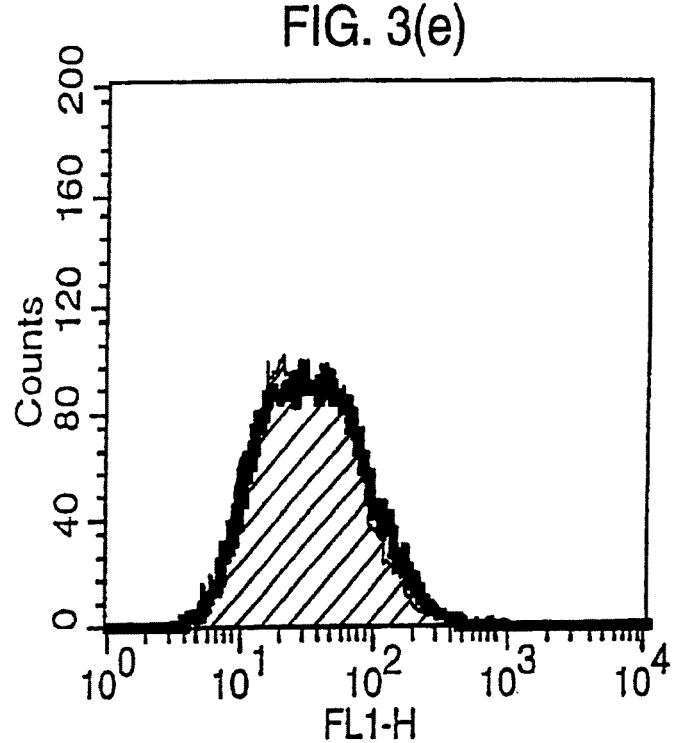
FIG. 3: shows surface phenotype of esDC grown is GM-CSF and IL-3 assessed by flow cytometry; Surface phenotype of esDC grown is GM-CSF and IL-3 assessed by flow cytometry. Filled histograms indicate levels of expression of CD44 (a), B7-1 (b), ICAM-1 (c) B7-2 (d), CD40 (e), CD11c (f) and class II MHC (g). Open histograms represent levels of background staining determined using irrelevant species- and isotype-matched control antibodies.
Figure 3F:
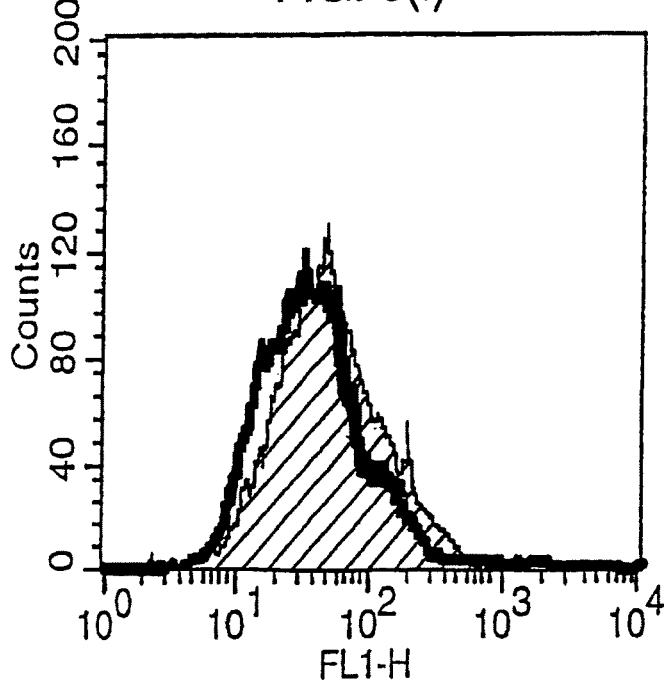

Although irregular morphology is a universal characteristic of DC, a novel source of cells cannot be unequivocally assigned to the DC lineage without recourse to determining their surface phenotype and functional potential. We have, therefore, prepared esDC as described and analysed their expression of surface markers by flow cytometry. Using a panel of monoclonal antibodies, we have shown esDC to express high levels of CD44 (FIG. 3a), indicative of their myeloid origin, and the presence of low but reproducible levels of the co-stimulatory molecules B7-1 (FIG. 3b) and ICAM-1 (FIG. 3c). Although neither B7-2 nor CD40 could be detected at the cell surface (FIG. 3d-e), analysis of mRNA by RT-PCR confirmed the presence of species specific for both molecules, as well as the DC-associated cytokines IL-12 and IL-18 (data not shown). Surprisingly, esDC lacked surface expression of both the DC-specific marker, CD11c (FIG. 3f), and MHC class II determinants (I-E$^K$) (FIG. 3g), a phenotype suggestive of their immature status.

2. Activity

Figure 4:
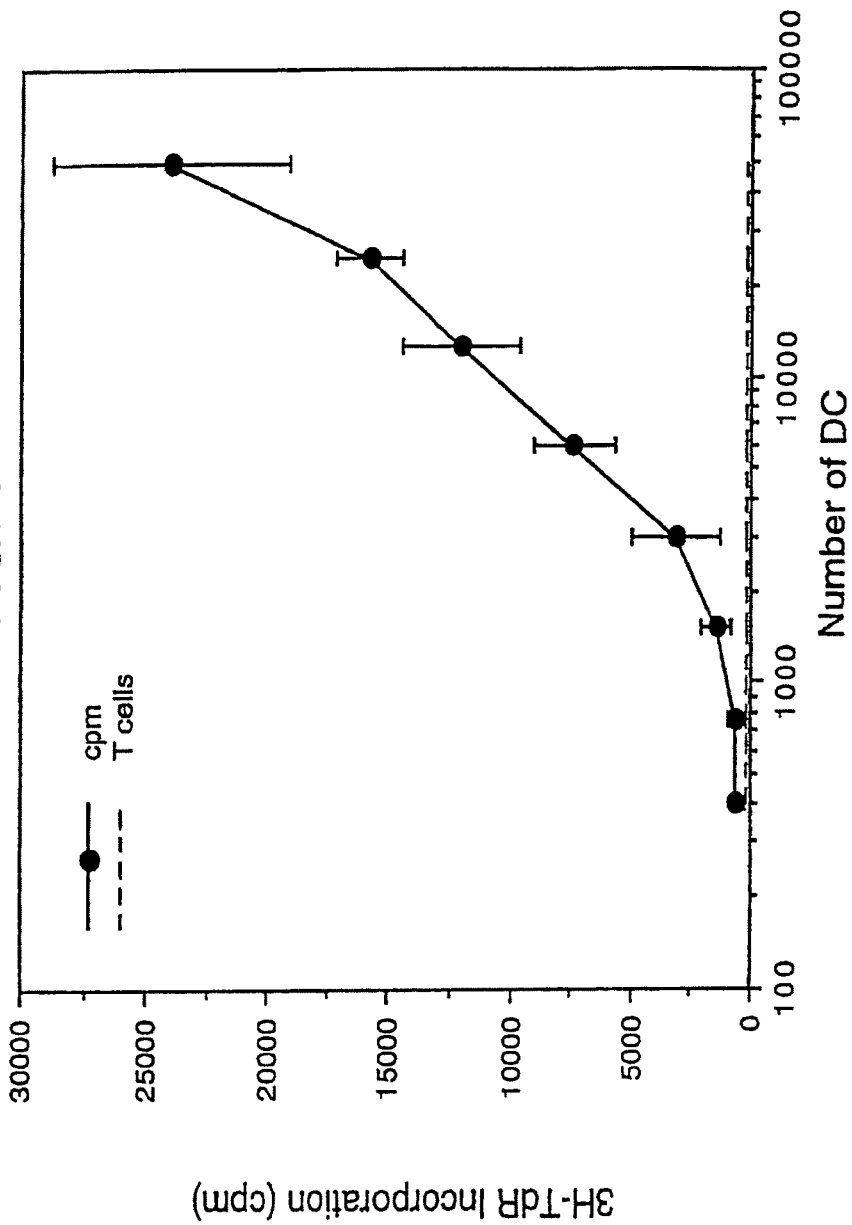
FIG. 4: shows immunostimulatory activity of esDC in the allogeneic mixed leukocyte reaction; Immunostimulatory activity of esDC in the allogeneic MLR. esDC from the CBA/Ca ES cell line ESF116 were co-cultured with purified T cells form C57B1/10 mice and the extent of proliferation was measured as a function of $^3$H-TdR uptake 5 days later.

Given the potential for expression of many co-stimulatory molecules by esDC, we investigated their ability to stimulate a primary T cell response, a function which distinguishes DC from all other APC. Accordingly, incubation of esDC with purified naive T cells from allogeneic C57B1/10 mice stimulated their proliferation in a dose-dependent fashion (FIG. 4), albeit with kinetics delayed by two days relative to mixed leukocyte reactions (MLRs) involving conventional sources of DC, such as the spleen and bone marrow. These findings were again suggestive of the immaturity of esDC which appeared to require several days for the acquisition of an immunostimulatory phenotype.

Since immature DC may be distinguished from mature cells by their greater propensity for antigen processing and presentation, we next investigated the ability of esDC to process the is classical foreign antigen, hen eggwhite lysozyme (HEL), for presentation to the T cell hybridoma, 2G7.1, known to be specific for the 1-18 peptide of HEL in the context of I-E$^K$ [Adorini et al., 1993]. Incubation of esDC with 2G7.1 induced their activation in an antigen-dependent fashion, leading to the active release of IL-2 (FIG. 5a). This activation was inhibited, either by the prior fixation of esDC with paraformaldehyde to prevent antigen up-take (FIG. 5a), or by the addition of a monoclonal antibody specific for I-E$^K$ (clone 17-3-3S) (FIG. 5b). These results suggest that, although immature at the time of harvesting, esDC are induced to mature and express class II MHC determinants upon interaction with T cells, similar requirements for T cell contact having been reported previously for the maturation of a DC line [Volkmann et al., 1996].

3. Maturation of esDC

Although engagement with T cells in a cognate fashion is the most potent stimulus currently known for DC maturation, studies from various laboratories have reported the additional role played by inflammatory mediators such as tumour necrosis factor a (TNF-a) and lipopolysaccharide (LPS) in the acquisition of an immunostimulatory phenotype. We investigated, therefore, whether the addition of LPS to cultures of esDC would act as a surrogate stimulus for their maturation in vitro, permitting the production of purified populations of immunostimulatory esDC that might be exploited for the purpose of vaccination.

Figure 6C:
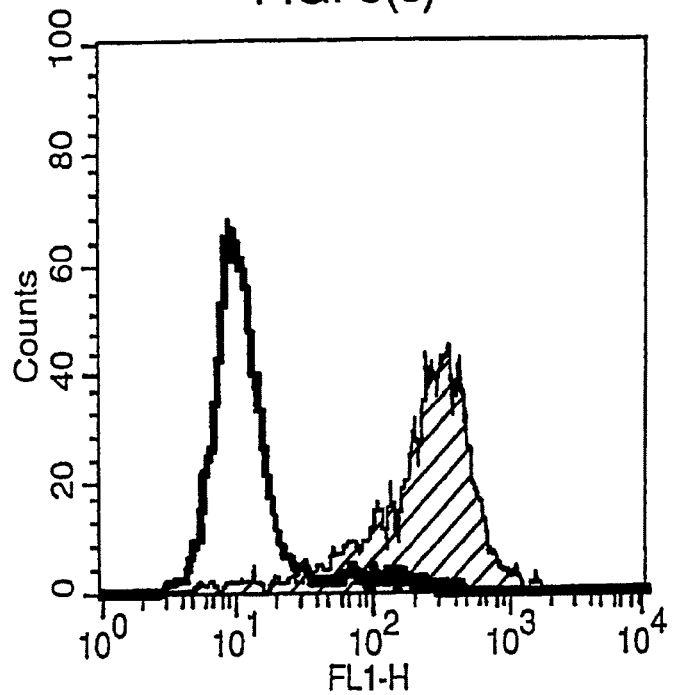
FIG. 6: shows flow cytometric analysis of esDC following maturation induced by the addition of LPS to cultures; Flow cytometric analysis of esDC following maturation induced by the addition of LPS to cultures. Filled histograms indicated the levels of expression of class II MHC (a), CD11c (b), B7-1 (c), B7-2 (d), CD40 (e) and ICAM-1 (f). Open histograms indicate the levels of background staining obtained using irrelevant species and isotype-matched control antibodies.
Figure 6D:
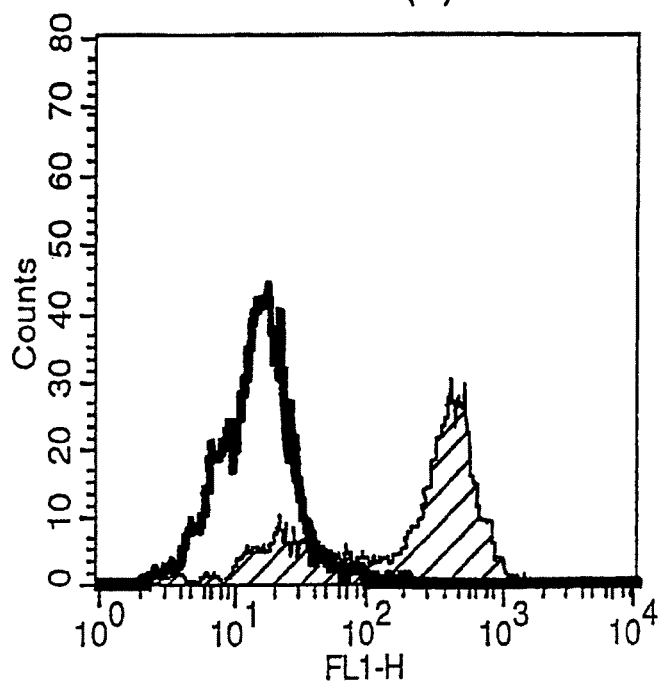
Figure 6E:
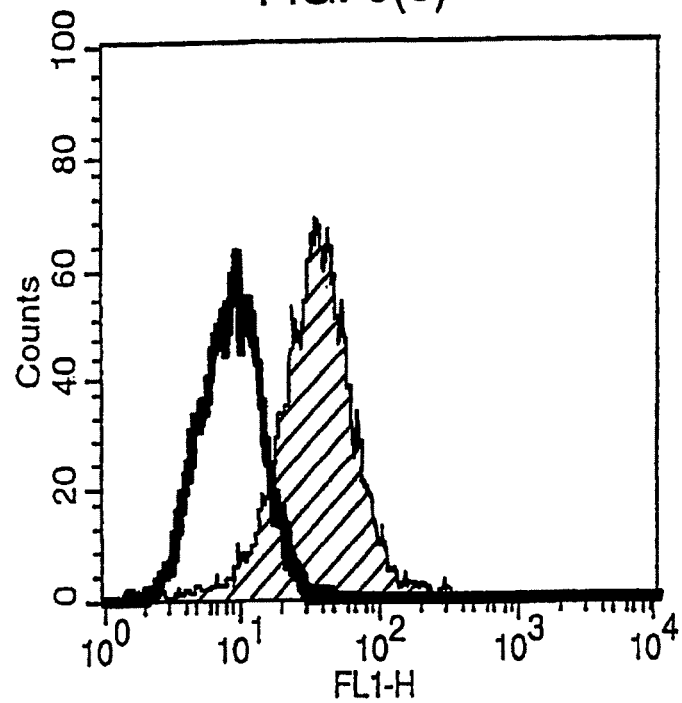
Figure 6F:
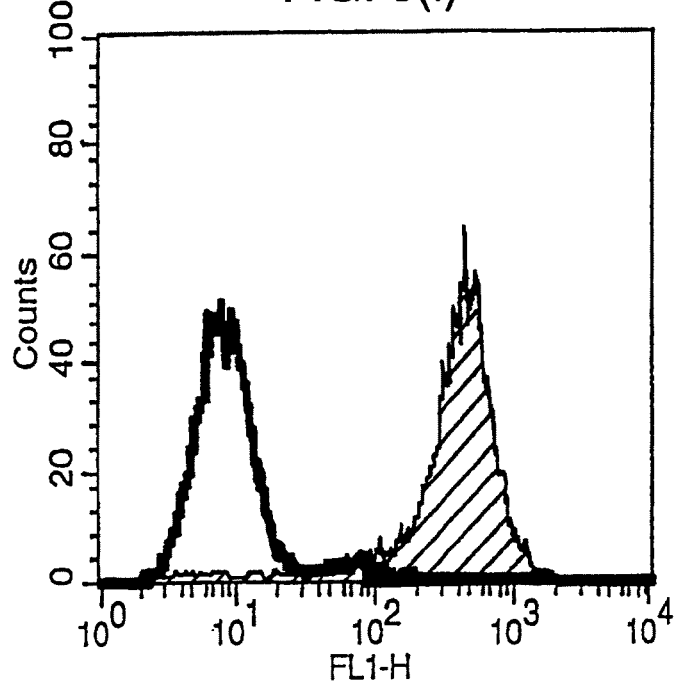

Accordingly, esDC were harvested and replated onto fresh tissue culture plastic in the presence of 1 µg/ml of LPS (Sigma). After overnight culture, many esDC had acquired a highly irregular morphology with large veils of cytoplasm and dendrites, characteristic of mature DC. Flow cytometric analysis revealed this population to have strongly up-regulated class II MHC (FIG. 6a) and the co-stimulatory molecules B7-1 (FIG. 6c), B7-2 (FIG. 6d), CD40 (FIG. 6e) and ICAM-1 (FIG. 6f). Furthermore, these DC expressed low but reproducible levels of CD11c (FIG. 6b), consistent with their acquisition of a mature phenotype.

Figure 7:
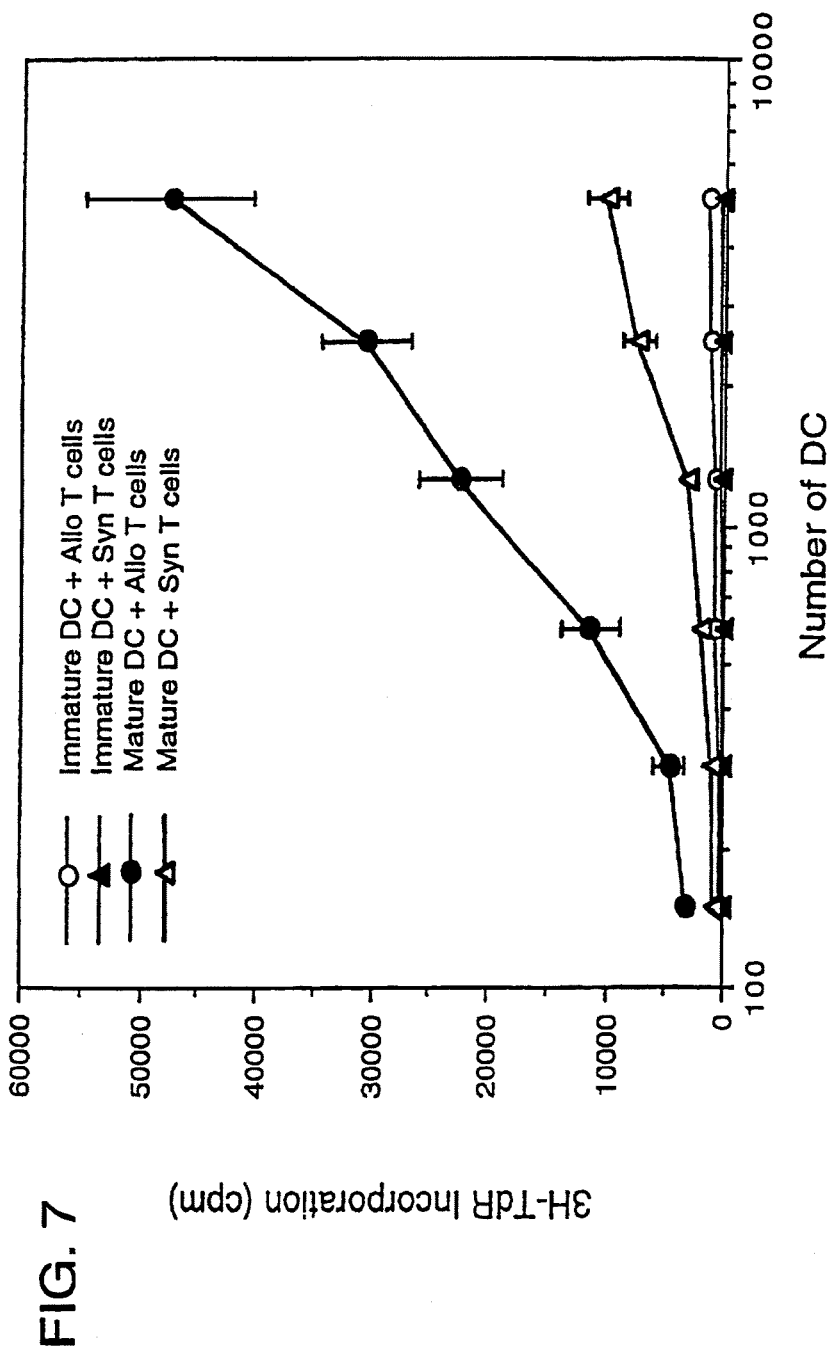
FIG. 7: shows immunostimulatory activity of LPS-treated esDC. Immunostimulatory activity of LPS-treated esDC. Mature esDC stimulate the strong proliferation of naive, allogeneic T cells (closed circles) only weak proliferation of syngeneic cells (open triangles). At the same time point, equivalent numbers of immature esDC fail to stimulate either allogeneic or syngeneic cells (open circles and closed triangles respectively).

When LPS-treated esDC were used as the stimulators of an MLR, they were found to induce the proliferation of allogeneic, but not syngeneic, T cells with enhanced kinetics (FIG. 7), the response peaking 48 hours earlier than was evident in cultures employing immature esDC as stimulators. Furthermore, responses significantly above background were obtained with as few as 600 esDC per well (FIG. 7), suggesting that, on a cell-by-cell basis, mature esDC are several orders of magnitude more potent in their capacity to induce primary T cell responses than their immature counterparts.

4. Lymphoid DC

Figure 8:
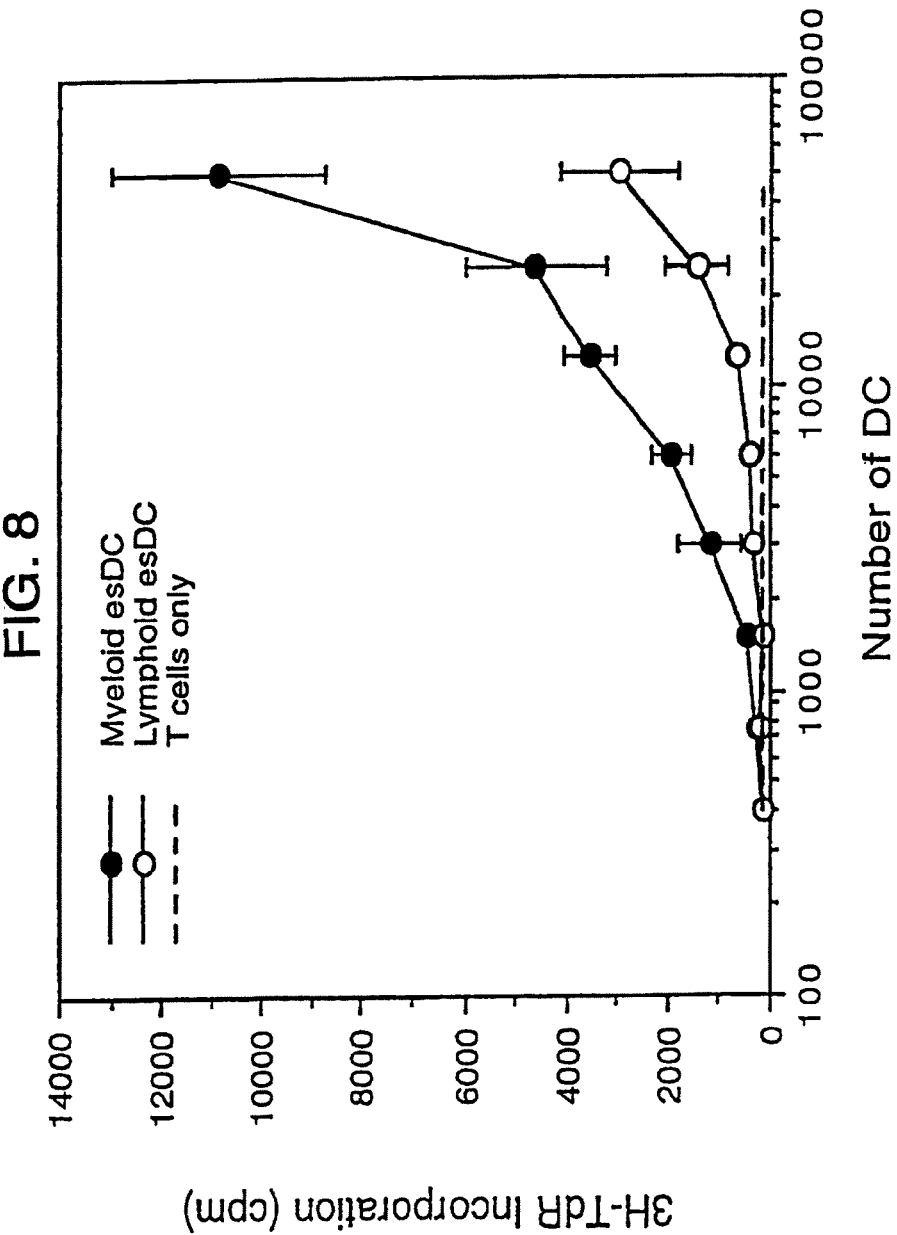
FIG. 8: shows Immunostimulatory activity by myeloid and lymphoid esDC; A comparison of the immunostimulatory activity of myeloid (closed circles) and 'lymphoid' esDC (open circles).
Figure 9:
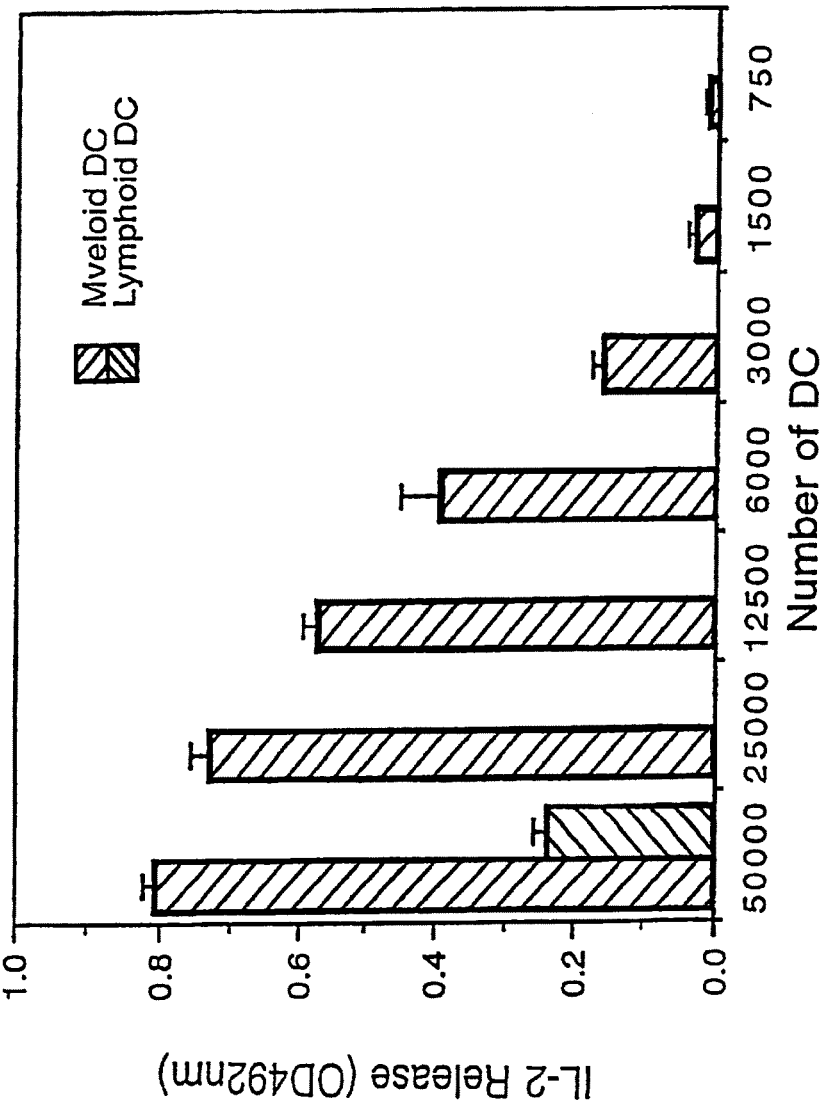
FIG. 9: shows antigen-processing activity of myeloid and lymphoid esDC. A comparison of the antigen-processing activity of myeloid and lymphoid esDC. At the top dose of DC, the lymphoid population (hatched bar) are considerably less able to present antigen to the hybridoma than myeloid DC (filled bar), although both induce widespread cell death.

We have investigated the functional phenotype of the putative lymphoid DC cultured in IL-3 alone. These cells are less capable of stimulating naive T cells in an MLR compared with esDC grown in a combination of GM-CSF and IL-3 (FIG. 8). Furthermore, although they retain residual capacity to process and present HEL to the 2G7.1 hybridoma (FIG. 9), they induce widespread apoptotic cell death of the responding T cells, far more than might be expected from the low level of activation indicated by IL-2 release. These data are consistent with the indications that DC cultured in IL-3 alone are closely allied to the lymphoid lineage, actively restricting T-cell responsiveness by initiating Fas-induced apoptosis.

Example 5

Genetic Modification of esDC—Transfection of ESF116 with Green Fluorescent Protein (GFP)

The ability to generate long-term cultures of primary DC from ES cells in vitro, provides unparalleled opportunities for the genetic modification of DC for use in immunotherapy.

ESF116 was transfected with an expression vector containing GFP and a stable clone is expressing high levels of the transgene was selected for the generation of esDC. The production of green fluorescent esDC will enable their migration patterns to be studied in vivo. The mammalian expression vector pEGFP-N1, used in these experiments, is commercially available (Clontech Catalogue Number: 6085-1; Genbank Accession Number: U55762) and contains a multiple cloning site designed to facilitate the production of fusion proteins between heterologous proteins and EGFP at the N-terminus. EGFP or fusion constructs are expressed under the control of the immediate-early promoter of human cytomegalovirus (CMV). The vector contains a neomycin resistance gene which provides G418 resistance for selection of stably transfected mammalian cells.

ESF116 were cultured away from fibroblast feeder cells using recombinant LIF and were harvested as a single cell suspension which was adjusted to $2 \times 10^6$ cells/ml. 800 µl of cell suspension were mixed with 40 µl of pEGFP-N1 at 1 µg/ml which had previously been linearized by incubation with the restriction endonuclease ApaL1 (BioLabs) for 3 hrs at 37° C. ESF116 were electroplated using 450V, a capacitance of 25 µF and a time constant of 0.5 sec and were placed on ice for 10 min. The cells were then distributed equally into two 25 cm² tissue culture flasks containing monolayers of embryonic fibroblasts derived from Rosa-26 mice, transgenic for the neomycin resistance gene. Selection was applied from 48 hrs onwards by the addition of 400 µg/ml of G418.

A single colony of ESF116 was obtained expressing high levels of GFP (FIG. 10a) which could easily be distinguished above the background autofluorescence of the fibroblast feeder cells (FIG. 10b). These transfected ES cells were used to generate embryoid bodies using our conventional protocol, with the exception that 400 µg/ml of G418 were added throughout the culture period. Embryoid bodies were screened using confocal fluorescence microscopy at various stages during their development and were found to retain expression of GFP throughout (FIG. 10c-d). After plating onto tissue culture plastic in the presence of GM-CSF and IL-3, dendritic cells were found to develop which continued to express the EGFP transgene introduced into the parent ES cell line (FIG. 10e-f). These results demonstrate the feasibility of introducing heterologous genes into DC for use in immunotherapy.

Example 6

Transfection of ESF116 with GFP Under the Control of the CD11c Promoter

Since upregulation of CD11c occurs during the maturation of DC, the expression of EGFP under the control of the CD11c promoter will enable the conditions for their maturation to be investigated. In order to prepare a suitable construct, the vector pBSCD11cβglob was obtained. This vector consists of an expression cassette composed of a 5.3 kb genomic fragment containing the murine CD11c promoter and a rabbit β globin fragment of approximately 1.2 kb providing an intron, all of which is cloned into the pBSbluescript vector (Stratagene) [Kouskoff et al., 1993, Brocker et al., 1997]. The resulting construct contains a unique EcoRl cloning site and a polyadenylation signal.

A ~1.8 kb PGKneopA cassette, consisting of the murine phosphoglycerate kinase-1 promoter and polyadenylation signals driving expression of a neomycin resistance gene, was cloned into the XhoI blunt site of pBSCD11cβglob to generate pBSCD11cβglob (neo). This cassette provides G418 resistance for selection of stably transformed cells. The cassette was inserted downstream of the CD11cβglob cassette to avoid any possibility of interference with the DC specificity of the CD11c promoter elements, and was cloned in the same orientation as the CD11cβglob cassette to avoid interference between the two and ensure that any run-through from the CD11cβglob cassette will result only in increased neomycin resistance.

EGFP was subcloned from pEGFP-N1 as a Bglll/Notl blunt fragment to the EcORl blunt site of the CD11cβglob cassette in pBSCD11cβglob (neo). The majority of the pEGFP-N1 multiple cloning site was retained to facilitate the future generation of heterologous proteins is fused to the N-terminus of EGFP under the control of the CD11cβglob expression cassette. Xhol and EcoRl are suitable cloning sites for the generation of such fusion constructs. The vector may be linearized using Notl or Xbal, other potential linearization sites being Scal and Xmnl in the pBS vector sequence.

Example 7

Transfection of ESF116 with Fas-Ligand Gene

Constructs were prepared for the introduction of the Fas-ligand gene (accession number: U58995) into ESF116 so as to generate DC constitutively expressing the protein. When administered to mice across an MHC barrier, these cells can be expected to attract naive T cells specific for the alloantigens they present: on activation, however, such cells will be targeted for apoptosis by ligation of cell surface Fas. This strategy may deplete an animal of alloreactive T cells allowing the subsequent acceptance of an organ allograft in spite of histoincompatibility.

REFERENCES

Adorini L et al. (1993) Processing of endogenously synthesized hen eggwhite lysozyme retained in the endoplasmic reticulum or in secretory form gives rise to a similar but not identical set of epitopes recognized by class II-restricted T cells. *J Immunol* 151:3576-3586

Albert M L et al. (1998a) Dendritic cells acquire antigen from apoptotic cells and induce class I-restricted CTLs. *Nature* 392:86-89

Albert M L et al. (1998b) Immature dendritic cells phagocytose apoptotic cells via □ᵥ□₅ and CD36 and cross-present antigens to cytotoxic T cells. *J Exp Med* 188:1359-1368

Austyn J M and Larsen C P (1990) Migration patterns of dendritic leukocytes. *Transplanation* 49:1-7

Banchereau J and Steinman R M (1998) Dendritic cells and the control of immunity. *Nature* 392:245-252

Boczkowski D et al. (1996) Dendritic cells pulsed with RNA are potent antigen-presenting cells in vitro and in vivo. *J Exp Med* 184:465-472

Brocker T, et al. (1997) Targeted expression of major histocompatibility complex (MHC) class II molecules demonstrates that dendritic cells can induce negative but not positive selection of thymocytes in vivo. *J Exp Med* 185:541-550

Brook F A and Gardner R L (1997) The origin and efficient derivation of embryonic stem cells in the mouse. *Proc Natl Acad Sci USA* 94:5709-5712

Cella M et al. (1996) Ligation of CD40 on dendritic cells triggers production of high levels of IL-12 and enhances T cell stimulatory capacity: T-T help via APC activation. *J Exp Med* 184:747-752

Cella M et al. (1997) Inflammatory stimuli induce accumulation of MHC class II complexes on dendritic cells. *Nature* 388:782-787

Celluzzi C M et al. (1996) Peptide-pulsed dendritic cells induce antigen-specific CTL-mediated protective immunity. *J Exp Med* 183:283-287

De Smedt T et al. (1996) Regulation of dendritic cell numbers and maturation by lipopolysaccharide in vivo. *J Exp Med* 184:1413-1424

Evans M J et al. (1997) Gene trapping and functional genomics. *Trends Genet* 13:370-374

Finkelmann F D et al. (1996) Dendritic cells can present antigen in vivo in a tolerogenic or immunogenic fashion. *J Immunol* 157:1406-1414

Fraichard A et al. (1995) In vitro differentiation of embryoinic stem cells into glial cells and functional neurons. *J Cell Sci* 108:3181-3188

Fung-Leung W-P and Mak T W (1992) Embryonic stem cells and homologous recombination. *Cur Opin Immunol* 4:189-194

Gardner R L (1985) Regeneration of endoderm from primitive ectoderm: fact or artifact? *J Embryol Morph* 88:303-326

Girolomoni G et al. (1995) Establishment of a cell line with features of early dendritic cell precursors from fetal mouse skin. *Eur J Immunol* 25:2163-2169

Goulet J L et al. (1997) Embryonic stem cell lines from MRL mice allow genetic modification in a murine model of autoimmune disease. *J Immunol* 159:4376-4381

Grouard G et al. (1997) The enigmatic plasmacytoid T cells develop into dendritic cells with IL-3 and CD40-ligand. *J Exp Med* 185:1101-1111

Gutierrez-Ramos J C and Palacios R (1992) In vitro differentiation of embryonic stem cells into lymphocyte precursors able to generate T and B lymphocytes in vivo. *Proc Natl Acad Sci USA* 89:9171-9175

Hakem R et al. (1998) Differential requirement for caspase 9 in apoptotic pathways in vivo. *Cell* 94:339-352

Hockenbery D et al. (1990) Bcl-2 is an inner mitochondrial membrane protein that blocks programmed cell death. *Nature* 348:334-336

Inaba K et al. (1992) Generation of large numbers of dendritic cells from mouse bone marrow cultures supplemented with GM-CSF. *J Exp Med* 176:1693-1702

Keller G et al. (1993) Hematopoietic commitment driving embryonic stem cell differentiation in culture. *Mol Cell Biol* 13:473-486

Keller G M (1995) In vitro differentiation of embryonic stem cells. *Cur Opin Immunol* 7:862-869

Koch F et al. (1996) High level IL-12 production by murine dendritic cells: upregulation via MHC class 11 and CD40 molecules and downregulation by IL-4 and IL-10. *J Exp Med* 184:741-746

Koller B H and Smithies 0 (1992) Altering genes in animals by gene targeting. *Annu Rev Immunol* 10:705-730

Kouskoff V, et al. (1993) A vector driving the expression of foreign cDNAs in MHC class II-positive cells of transgenic mice. *Immunol Methods* 166:287-291

Kronin V et al. (1996) A subclass of dendritic cells regulates the response of naive CD8 T cells by limiting their IL-2 production. *J Immunol* 157:3819-3827

Lehmann P V et al. (1993) Determinant spreading and the dynamics of the autoimmune T cell repertoire. *Immunol Today* 14:203-208

Li M et al. (1998) Generation of purified neural precursors from embryonic stem cells by lineage selection. *Cur Biol* 8:971-974

Liblau R S et al. (1995) Th1 and Th2 CD4+ T cells in the pathogenesis of organ-specific autoimmune diseases. *Immunol Today* 16:34-38

Mayordomo J I et al. (1995) Bone marrow-derived dendritic cells pulsed with synthetic tumour specific peptides elicit protective and therapeutic antitumour immunity. *Nature Med* 1:1297-1302

Nishitani S et al. (1994) Lineage marker-negative lymphocyte precursors derived from embryonic stem cells in vitro differentiate into mature lymphocytes in viva. *Int Immunol* 6:909-916

Paglia P et al. (1993) Immortalized dendritic cell line fully competent in antigen presentation initiates primary T cell responses in vivo. *J Exp Med* 178:1893-1901

Palacios R et al. (1995) In vitro differentiation of hematopoietic stem cells from an embryonic stem cell line. *Proc Natl Acad Sci USA* 92:7530-7534

Potocnik A J et al. (1997) Hemato-lymphoid in vivo reconstitution potential of subpopulations derived from in vitro differentiated embryonic stem cells. *Proc Natl Acad Sci USA* 94:10295-10300

Saunders D et al. (1996) Dendritic cell development in culture from thymic precursor cells in the absence of granulocytel-macrophage colony stimulating factor. *J Exp Med* 184:2185-2196

Schmitt R M et al. (1991) Hematopoietic development of ES cells in vitro: cytokine and receptor gene expression. *Genes Develop* 5:728-740

Shortman K and Caux C (1997) Dendritic cell development: multiple pathways to nature's adjuvant. *Stem Cells* 15:409-419

Smith A G et al. (1988) Inhibition of pluripotential embryonic stem cell differentiation by purified polypeptides. *Nature* 336:688-690

Snodgrass H R et al (1992) Embryonic stem cells and In vitro Hematopoiesis. *J. Cellular Biochem.* 49: 225-230

Sonada Y et al. (1988) Analysis in serum free culture of the targets of recombinant human hemopoietic growth factors: interleukin 3 and granulocyte macrophage colony stimulating factor are specific for early developmental stages. *Proc Natl Acad Sci USA* 85:4360

Steinman R M and Cohn Z A (1973) Identification of a novel cell type in peripheral lymphoid organs of mice. I. Morphology, quantitation, tissue distribution. *J Exp Med* 137:1142-1162

Steinman R M (1991) The dendritic cell system and its role in immunogenicity. *Annu Rev Immunol* 9:271-296

Su H et al. (1998) Vaccination against Chiamydial genital tract infection after immunization with dendritic cells pulsed ex vivo with nonviable Chlamydiae. *J Exp Med* 188:809-818

Suss G and Shortman K (1996) A subclass of dendritic cells kills CD4 T cells via Fas-Fas ligand induced apoptosis. *J Exp Med* 183:1789-1796

Thomson A W et al. (1996) Dendritic cells and the balance between transplant tolerance and immunity. In: Immune Tolerance Elsevier, Paris. pp 173-185

Thomson J A et al. (1998) Embryonic stem cell lines derived from human blastocysts. *Science* 282:1145-1147

Velculescu V E et al. (1995) Serial analysis of gene expression. *Science* 270:484-487

Volkmann A et al. (1996) A conditionally immortalized dendritic cell line which differentiates in contact with T cells or T cell-derived cytokines. *Eur J Immunol* 26:2565-2572

Wakayama T et al. (1998) Full-term development of mice from enucleated oocytes injected with cumulus cell nuclei. *Nature* 394:369-374

Wiles M V and Keller G (1991) Multiple hematopoietic lineages develop from embryonic stem (ES) cells in culture. *Develop* 111:259-267

Wiles M V (1993) In vitro embryonic stem cell differentiation to mesoderm and hematopoietic cells. *Method Enzymol* 225:900-918

Wilmut I et al. (1997) Viable offspring derived from fetal and adult mammalian cells. *Nature* 385:64-66

Wu L et al. (1997) Cell-autonomous defects in dendritic cell populations of Ikaros mutant mice point to a developmental relationship with the lymphoid lineage. *Immunity* 7:483-492

Xu S et al. (1995) Successive generation of antigen-presenting, dendritic cell lines from murine epidermis. *J Immunol* 154:2697-2705

Zambrowicz B P et al. (1998) Disruption and sequence identification of 2000 genes in mouse embryonic stem cells. *Nature* 392:608-611

The invention claimed is:

1. A method of assessing the effect of a gene on a cultured dendritic cell, the method comprising:
   providing a genetically modified cultured es dendritic cell (esDC) expressing a heterologous gene, wherein the genetically modified cultured esDC is a dendritic cell that is obtained by culturing an embryonic stem cell in vitro;
   providing a cultured es dendritic cell (esDC), wherein the cultured esDC is a dendritic cell that is obtained by culturing an embryonic stem cell in vitro, wherein the cultured esDC is not genetically modified to express the heterologous gene; and
   assessing an effect of the heterologous gene on the genetically modified cultured esDC by comparing the genetically modified cultured esDC to the cultured esDC.

2. The method of claim 1, wherein the genetically modified cultured esDC and the cultured esDC are human esDC.

3. The method of claim 1, wherein genetically modified cultured esDC and the cultured esDC are mouse esDC.

4. The method of claim 1, wherein the heterologous gene encodes a protein which has an immunomodulatory effect.

5. The method of claim 1, wherein the heterologous gene encodes a cell surface receptor.

6. The method of claim 1, wherein the heterologous gene encodes Fas-ligand.

7. The method of claim 1, wherein the heterologous gene encodes a dominant negative form of an endogenous protein.

8. The method of claim 1, wherein the heterologous gene encodes an antigen target of the immune system.

9. The method of claim 8, wherein the antigen target of the immune system is an autoantigen.

10. The method of claim 8, wherein the antigen target of the immune system is a tumor antigen.

11. The method of claim 8, wherein the antigen target of the immune system is an antigen from an infectious agent.

12. The method of claim 8, wherein the antigen target of the immune system is a microbial antigen.

13. The method of claim 8, wherein the antigen target of the immune system is a viral antigen.

14. The method of claim 1, wherein the heterologous gene encodes an anti-apoptotic gene.

15. The method of claim 14, wherein the anti-apoptotic gene is FLIP or bcl-2.

16. The method of claim 1, wherein the heterologous gene encodes a fluorescent protein.

17. The method of claim 1, wherein the genetically modified cultured esDC co-expresses two or more heterologous genes.

18. The method of claim 1, wherein the genetically modified cultured esDC comprises one or more endogenous genes that have been inactivated.

19. The method of claim 18, wherein the endogenous gene that has been inactivated is selected from the group consisting of B7-1, IL-12, p35 subunit of IL-12, and the p40 subunit of IL-12.

* * * * *